(12) United States Patent
Pearlman

(10) Patent No.: US 7,209,835 B1
(45) Date of Patent: Apr. 24, 2007

(54) ALGORITHMIC TESTING IN LABORATORY MEDICINE

(75) Inventor: Eugene S. Pearlman, New York, NY (US)

(73) Assignee: Centralized Laboratory Services, Inc., Long Island City, NY (US)

( * ) Notice: Subject to any disclaimer, the term of this patent is extended or adjusted under 35 U.S.C. 154(b) by 0 days.

(21) Appl. No.: 09/303,315

(22) Filed: Apr. 30, 1999

(51) Int. Cl.
*G06F 19/00* (2006.01)
*G01N 33/50* (2006.01)

(52) U.S. Cl. .............................. 702/19; 702/20; 706/54
(58) Field of Classification Search ................. 702/19, 702/20; 706/54
See application file for complete search history.

(56) References Cited

U.S. PATENT DOCUMENTS 6,099,469 A * 8/2000 Armstrong et al. ......... 600/300
6,140,065 A * 10/2000 Carlson et al. ............. 435/7.23
6,270,963 B1 * 8/2001 Stevens et al. ................ 435/6

OTHER PUBLICATIONS

Adlassnig et al. (Artificial Intelligence in Medicine, 1995, vol. 7, pp. 1-24).*
Pearlman et al. (Clin. Lab. Manage. Rev. 1998 (Jul.-Aug.) vol. 12, No. 4, pp. 243-247).*
McGovern P.G. et al., 1996, N. Eng. J. Med. 334:884.
Agewall S. et al., 1998, J. Hypertension 16:1555.
Refsum H. et al., 1998, Annu. Rev. Med. 49:31.
Ridker P. M. et al., 1998, Circulation 98:731.
Fujiwara K. et al., 1998, Dig. Dis. Sci. 43:368.
Incident Investigation Team, 1997, N. Eng. J. Med. 336:178.
Ginsburg K.S. et al., 1992, Ann Int. Med. 177:997.
Finazzi et al., 1996 Am J. Med. 100: 530.
Srinand et al. Algorithmic approach to high-throughout molecular screening for alpha interferon-resistant genotypes in hepatitis C. patients. Journal of Clinical Microbiology. Jul. 1998, vol. 36, No. 7, pp. 1895-1901, see entire article.
Auffermann et al. Rapid diagnostic DNA cytometry with an automatic microscope and a TV image-analysis system. Analytical Quantitative Cytology, 1984, vol. 6, No. pp. 179-188, see entire article.
Okada et al. Medical data base system with an ability of automated diagnosis. Computer Programs Biomed. 1977, vol. 7, No. 3, pp. 163-170, see entire article.
Silver et al. The predictive and explanatory power of inductive decision trees: A comparison with artificial neural network learning as applied to the noninvasive diagnosis of coronary artery disease. Journal of Investigative Medicine. Feb. 1997, vol. 45, No. 2, ages 99-108, see entire article.
Beksac et al. An artificial intelligent diagnostic system for the interpretation of umbilical artery blood flow velocity waveforms. European J. Obstet. Gynecol. Reprod. Biol. 1966, vol. 64, pp. 37-42, see entire article.

* cited by examiner

*Primary Examiner*—Marjorie A. Moran
*Assistant Examiner*—Lori A. Clow
(74) *Attorney, Agent, or Firm*—Rashide A. Karmali

(57) ABSTRACT

A method of pipelining a disease specific diagnostic algorithm on an n-bit data word stored in a memory whereby the n-bit data word is divided into clinical tests describing ranges of normal values. Then, each of the clinical tests of the n-bit data word is read out from memory. Upon receiving a first of the results of the clinical tests, the result is compared with the normal value and the detection algorithm is computed based on the first result. This results in continuation with the next test if positive or terminate if negative. The above-steps are repeated recursively until all of the required test in the diagnostic algorithm are computed to provide the complete diagnosis of a disease.

1 Claim, 18 Drawing Sheets

ALGORITHMIC TESTING IN LABORATORY MEDICINE

BACKGROUND OF THE INVENTION

The present invention relates generally to programmable automation of systems and devices used in a clinical laboratory, whereby an intelligent automation is introduced into an algorithm to allow the systems and devices to self-monitor after performing a first assay and to proceed with analysis of second and subsequent tier assays based on the results of tests done at the preceding stage of the algorithm. The method allows the system to respond appropriately to preceding results and eliminate tasks and assays that are unnecessary. In the practice of the invention, the algorithm provides a step-by-step procedure whereby only the relevant assays are carried out in sequence providing result of performed tests which are both rapid, complete and cost-effective.

The worldwide efforts to reduce the overall costs of medical care through the introduction of managed care and other strategic approaches have caused many clinical laboratories to consolidate into larger, more efficient entities that are aiming to implement wide-scale automation. The principles that are applied to automate the analytical process in clinical laboratories include, commercially available chemistry, hematology, immunoassay, nucleic acid systems, point-of-care analyzers and automated specimen processing systems. The development of automated instruments has enabled laboratories to process a much larger workload without a comparable increase in staff. Another benefit of automation is the reduction in the variability of results and errors of analysis of eliminating tasks that are repetitive and monotonous for a human and that can lead to inattention. The improved reproducibility and quality of laboratory tests thus owes much to the combination of well designed automated instrumentation with good analytical methods and effective quality assurance programs.

Automation has resulted in substantial cost savings because of the reduction in the number of staff needed to process the clinical test workload. However, these substantial cost savings have not had a significant impact on the overall cost of Medical care. In fact, the ease of automation may have indirectly resulted in ordering by prescription of a broad-spectrum of tests, including some unnecessary ones, rather than ordering selective tests that provide a complete diagnosis of a disease. In addition, the increasing fear of malpractice charges for misdiagnosis by the wary physician has encouraged an indiscriminate number of clinical tests to be ordered and carried out. Thus, there is an urgent need to develop systems that measure only the necessary assays but move between distinct modes of laboratory utilization without a prolonged transition period, to provide a complete and accurate diagnosis with the first procured sample.

SUMMARY OF THE INVENTION

In accordance with the invention, systems and methods are provided for algorithmic testing for evaluation of the pathological condition of a variety of diseases, pathogens, factors, and conditions including, but not limited to, acid-fast bacteria, anemia, cardiac risk, thrombophilia, hepatitis B antigen (HBsAg) for prenatal and dialysis specimens, breast cancer antigens, prostate cancer markers, Epstein-Barr Virus, different types of hepatitis, thyroid function, autoimmune diseases, serum protein factors, urinalysis, human immunodeficiency virus, hepatitis B, or syphilis.

The present invention provides methods for algorithmic testing in the clinical laboratory whereby intelligent automation is introduced into an algorithm to allow the systems to self-monitor after performing each assay and determine the sequence and type of the next assay based upon the results just obtained. The method can select the next appropriate test to be carried out and eliminates the unnecessary tests. The system also allows movement between distinct modes of laboratory utilization without a prolonged transition period.

The present invention also provides algorithmic or reflexive testing for clinical tests which proceeds to the (n+1)st assay in a test sequence depending on the outcome of the nth test results, even for moderate test volumes, by intelligent programming of a computer device, wherein the program orders the next test in a particular progression only if the result on the prior assay falls outside of a prespecified range stored in memory.

In general in one aspect, the invention is a method of pipelining a disease-specific algorithm on an intrinsic part of the architecture of the laboratory computer system. System includes an event-driven, expert rule based, decision-support software within the Cerner System. It includes the step of: a) carrying out the first test and storing the result obtained in the expert system; b) computing the next test necessary in the algorithm using the information stored for the normal values and comparing the result of the first test; c) computing the next portion of the algorithm using the most recently obtained result; d) comparing the second result with normal values stored in the memory of the processor; and e) if necessary continuing recursively the next set of tests in sequence, until a final diagnosis is processed, wherein the final read-out produced by the computer includes all of the results obtained during various clinical tests carried out in the algorithm.

In general, in another aspect, the invention is an apparatus for pipelining a disease specific detection algorithm on an n-bit data word. The apparatus includes a) memory storing the n-bit data word; b) means for sequentially reading out each of a m series of the n-bit data word from the memory, wherein m is an integer than one; c) m tests each of which is programmed to compute a different test result in the diagnostic algorithm, wherein each of the tests after a first test receives the result from the prior stage and wherein the test result from a last of the m tests provides a complete diagnosis from the algorithm used.

In preferred embodiments, the m tests have an equal number of bits. The memory includes an array of chips, each of which includes a plurality of m bit storage cells.

In accordance with the invention, a system is provided for reflexive testing of a clinical specimen which continues the testing of the specimen to the second or higher-tier assays. In routine circumstances, a patient would be required to come for follow-up visits before such a second test is ordered by a physician, and for which a new specimen would have to be collected.

According to additional aspects of the invention, there is provided an in-house cost-accounting model that evaluates direct costs for each of the assays carried out and provides an overall cost reduction in testing of a specific specimen to completion.

According to yet another aspect of the present invention, there is provided a system to reflexively test a clinical specimen to its completion, based upon preset clinical reference standards, and expedites the rate and efficiency at which a patient receives the complete diagnosis of his or her condition.

The present invention also provides algorithmic testing which is rapid, efficient, accurate, selective and a much needed cost-saving strategy in medical care in general.

It is the object of the present invention to provide systems and methods for algorithmic testing of a clinical sample through intelligent automation to allow movement between distinct modes of laboratory utilization without a prolonged transition period.

It is also an object of the present invention to provide algorithmic testing for a clinical specimen which proceeds to the (n+1)st assay in a test sequence depending on the outcome of the nth test result, even for moderate test sample volumes.

It is another object of the present invention to provide a more rapid, accurate, relevant and cost-effective algorithmic system in any clinical laboratory.

Still other objects of the invention will, in part, be obvious and will, in part, be apparent from the specification.

The invention accordingly comprises the several steps and the relation of one or more of such steps with respect to each of the others, and the systems embodying features of intelligent programming, combination of processes which are adapted to affect such steps, all as exemplified in the following detailed disclosure and the scope of the invention will be indicated in the claims.

BRIEF DESCRIPTION OF THE DRAWINGS

For a fuller understanding of the invention, reference is had to the following description taken in connection with the accompanying drawings, in which.

The algorithm monitors HIV-1 and HIV-2.

Figure 16:
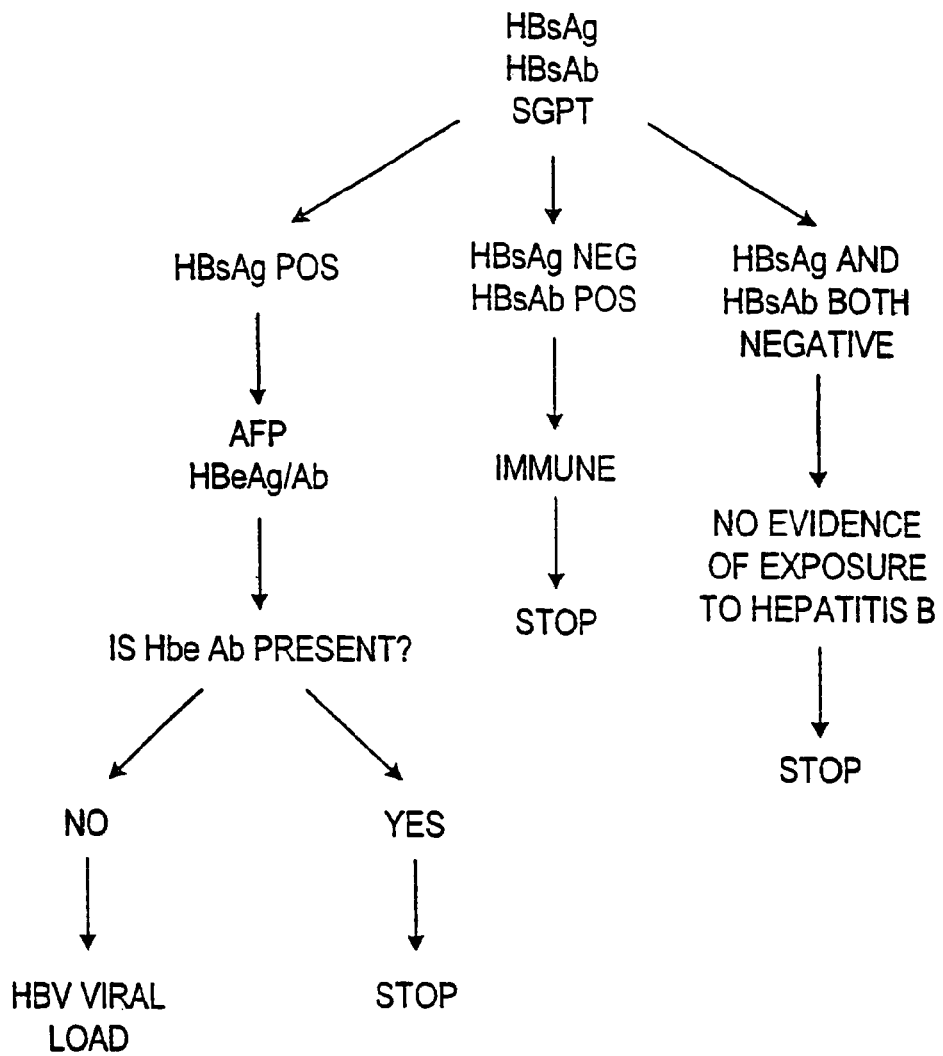

FIG. 16 is a diagram illustrating the hepatitis B algorithm with the follow-up (n+1)st test dependent on the result of the nth assay;

The algorithm measures HBsAg, HBSAb and SGPT.

Figure 17:
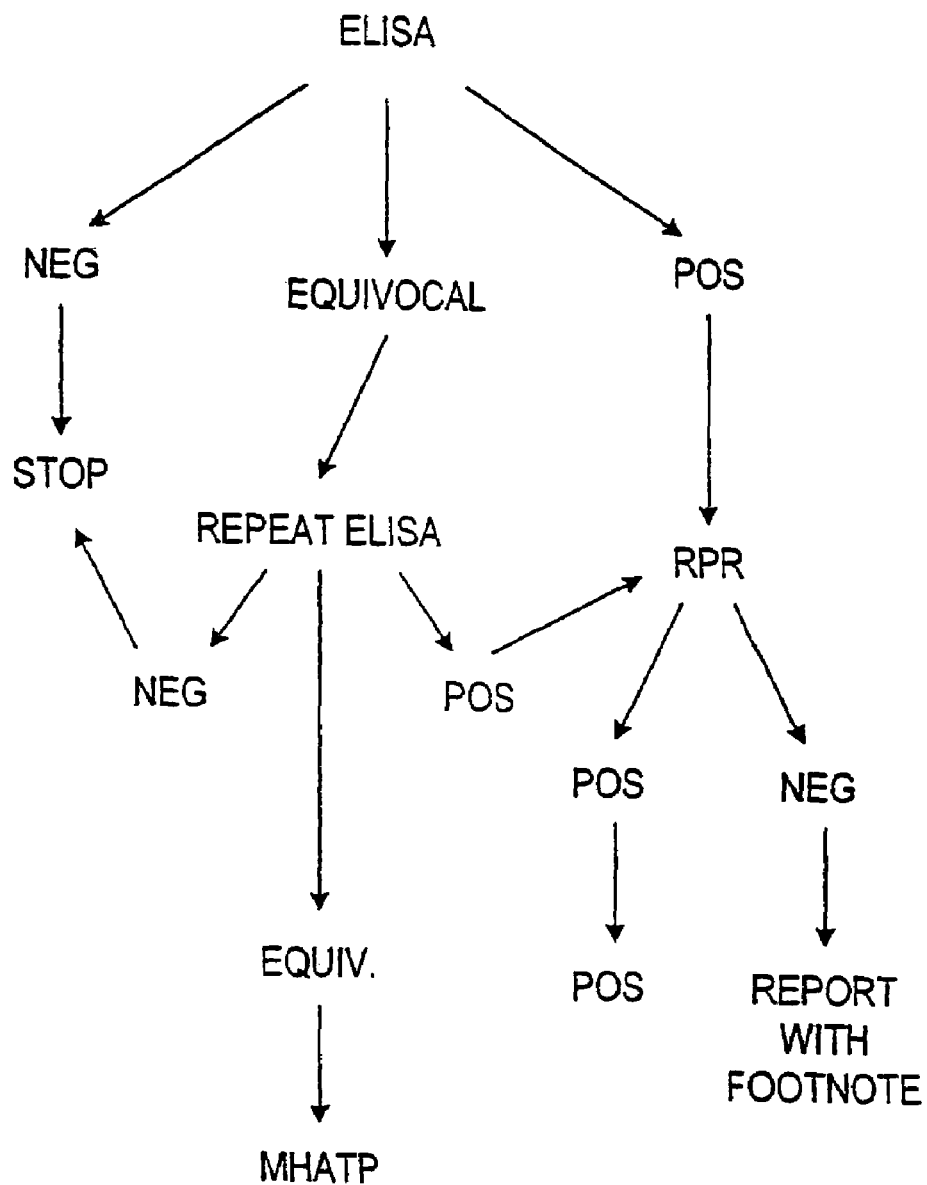

FIG. 17 is a diagram illustrating the syphilis algorithm with the follow-up (n+1)st test dependent on the result of the nth assay; the algorithm comprises an automated objective assay for specific antibodies against the specific organism Treponemal specific screen; the positive samples are reflexed to an RPR; a positive RPR is a useful guide to therapy; a negative RPR indicates a discrepancy and may indicate either previously treated or late stage syphilis.

Figure 18:
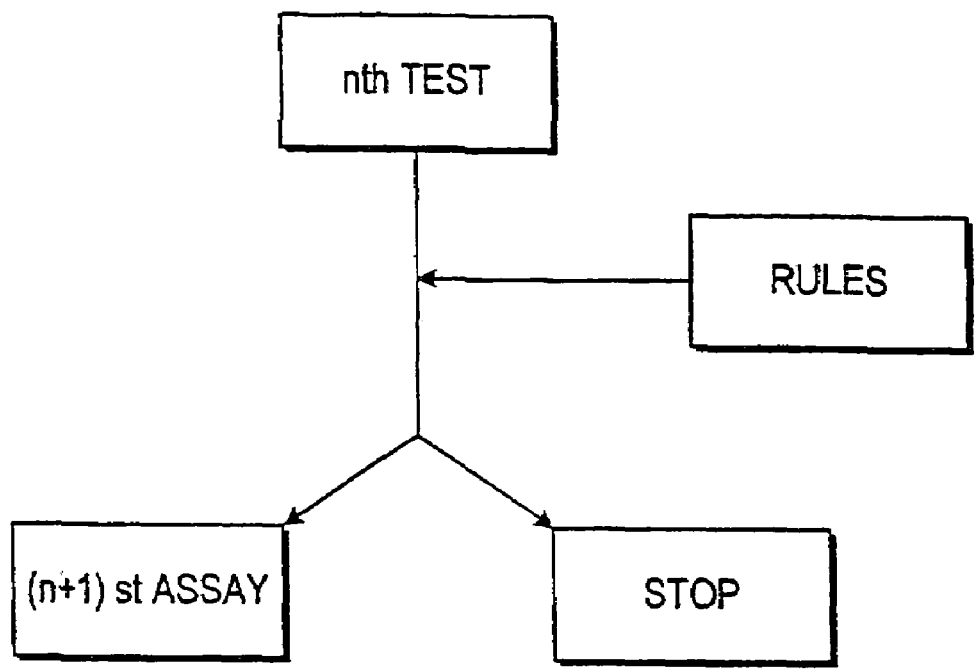

FIG. 18 is a schematic diagram of the digital signal processor executing an algorithmic procedure on an expert system which is an intrinsic part of the architecture of a laboratory computer system; the expert system is an event-driven, expert rule based, decision-support software within the Cerner System.

DETAILED DESCRIPTION OF THE PREFERRED EMBODIMENT

The present invention generally pertains to novel programmable algorithms used in a clinical laboratory, whereby methods for an intelligent automation allow the system to self-monitor and perform the (n+1)st assay based upon the results of nth test, thereby eliminating unnecessary tests and moving between distinct modes of laboratory utilization rapidly and in a cost-effective strategy.

4.1. Acid-Fast Bacteria Algorithm

*Mycobacteria* are difficult to stain. The large amount of lipids present in their cell walls render them impermeable to the dyes used in the Gram stain, and the appearance of mycobacteria in a Gram stained specimen may be variable. *Mycobacteria* may be gram invisible, they may appear as negatively stained images or ghosts, or they may appear as beaded gram-positive rods. *Mycobacteria* are able to form stable complexes with certain arylmethane dyes such as fuchsin and auramine O. Phenol in the primary stain allows penetration of the stain. The cell wall mycolic acid residues retain the primary stain even after exposure to acid-alcohol or strong mineral acids.

The acid-fast nature of an organism can be determined by several methods. In carbol fuchsin staining procedures, such as Ziehl-Neelsen and Kinyoun staining, AFB appear red against a blue or green background, depending on the counterstain used. In fluorochrome staining procedures, such as with auramine O or auramine-rhodamine, AFB fluoresce yellow to orange (the color may vary with the filter system used). Carbol fuchsin-stained smears are examined with a 100× oil immersion objective (×1,000 magnification) and a light microscope. Fluorochrome-stained smears can be scanned at ×150 to ×200 magnification with a fluorescence microscope, with confirmation of AFB morphology at ×450 or ×1,000 magnification. Because acid-fast artifacts may be present in a smear, it is necessary to view all morphology carefully.

Although the sensitivity of the direct acid-fast smear examination for the diagnosis of mycobacterial infection is lower than that of culture methods, the acid-fast smear has an important role in early diagnosis of mycobacterial infection because of the relatively long time required for mycobacteria to be detected by culture methods. It is important to detect the presence of mycobacterial disease as rapidly as possible for implementation of appropriate patient care and public health measures. The acid-fast stain also serves to confirm the acid-fast nature of organism recovered from culture and to monitor the effectiveness of antimycobacterial therapy. The quantitation of a positive smear is also used as an aid in the determination of appropriate dilutions of a specimen for direct susceptibility testing.

The overall sensitivity of direct acid-fast smear ranges from 22 to 80%. Factors influencing sensitivity include types of specimens examined, centrifugation speed, staining technique, culture method used, and patient population being evaluated. It is best to confirm positive smears by having them examined by another experienced reader.

Acid-fast stains may be used on any type of clinical materials or organisms recovered from cultures that are suspected to be mycobacteria. In laboratories that routinely culture for mycobacteria, smears from sputum and other respiratory tract secretions are usually prepared after concentration of the specimen. If rapid evaluation of a specimen is needed, a direct smear may be prepared from the purulent portion of the specimen; however, the sensitivity of this smear will be less than that of a concentrated specimen.

Figure 1:
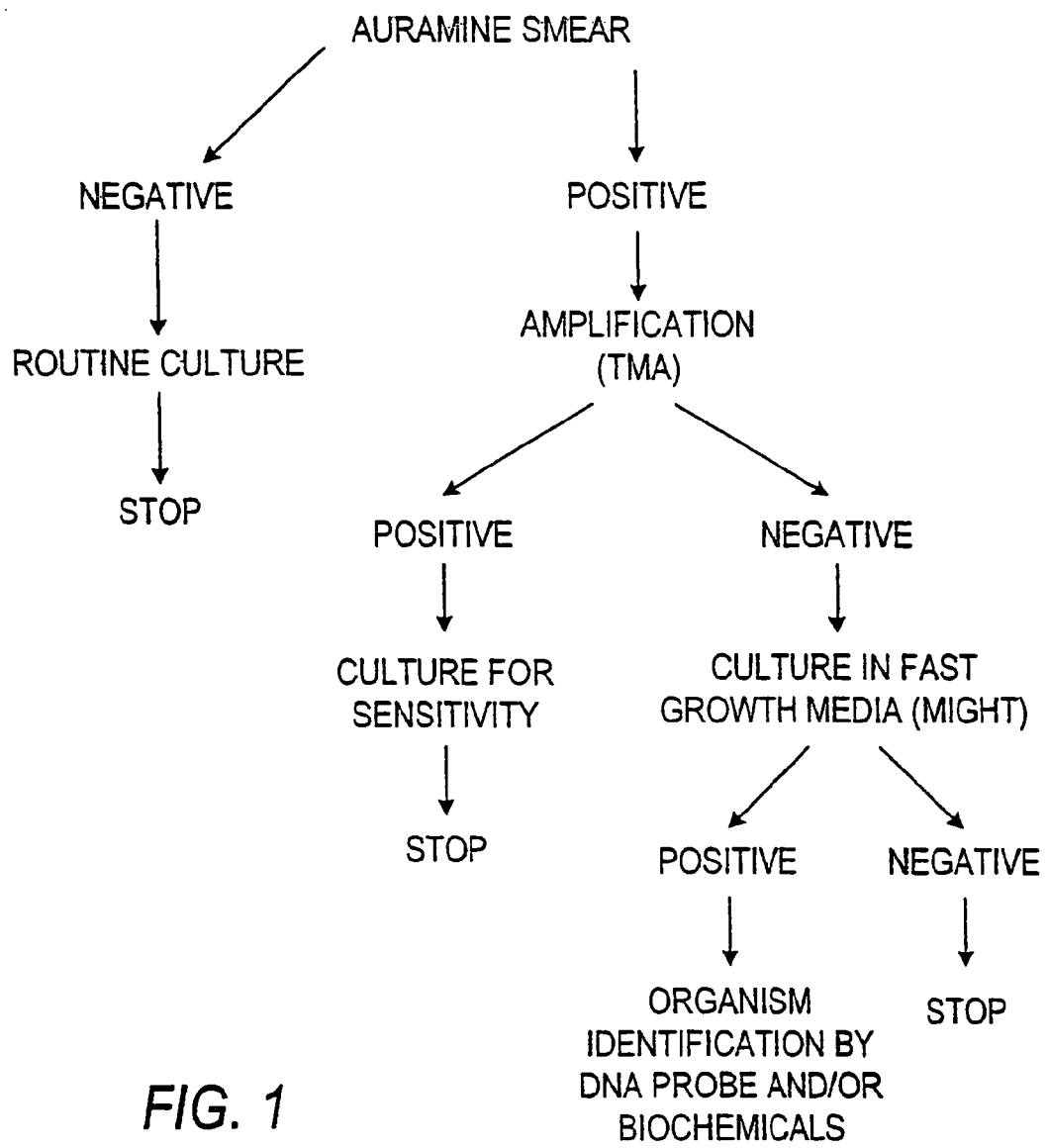
FIG. 1 is a diagram illustrating the acid-fast bacteria algorithm with the follow-up (n+1)st test dependent on the result of the nth assay; the algorithm comprises the steps of flurochrome staining, amplification, culture in fast growth and organism identification by DNA probe and/or biochemicals.

FIG. 1 describes an acid-fast algorithm, in particular for tuberculosis.

Tuberculosis has been long-standing public health problem which has again come into the limelight with the emergence of multi-drug resistant strains of *M. tuberculosis*. Public Health authorities have responded with directly observed therapy but there is general concensus that rapid diagnosis is essential to effective containment of infectious tuberculosis. Traditional approaches to the diagnosis of this disease have consisted of two steps.

a) A sputum slide stain with an "acid fast" or a flurochrome stain b) Culture of mycobacteria on special media.

Unfortunately not all mycobacteria which stain with "acid fast" stains cause tuberculosis. *M. gordonae* for example is non-pathogenic. Conventional culture takes up to six weeks before "no growth" can be diagnosed.

The introduction of molecular amplification technology has speeded up the diagnosis of tuberculosis but is a costly procedure. The CLS algorithm uses molecular amplification but only in smear positive cases. This allows early diagnosis in those instances in which a positive result is most likely. Smear (slide) negative cases are sent for routine culture. Smear positive but amplification negative specimens are placed into fast growth culture bottles (MGIT) in which mycobacteria can grow somewhat more rapidly than in conventional culture. Such MGIT bottles can save 1–2 weeks opposed to routine culture bottles.

Thus the algorithm of the present invention is a cost-effective approach to the rapid diagnosis of tuberculosis and meets important public health objectives.

REMEL's TB Base Digestant is a reagent recommended for use in qualitative procedures in the digestion/decontamination procedure for the isolation of *Mycobacterium* species.

The majority of clinical specimens submitted to the mycobacteriology laboratory for cultural confirmation of the etiologic agent are contaminated by more rapidly growing normal flora microorganisms. Also, much-trapped mycobacterial cells may not be released for culture; therefore liquefaction of certain specimens, particularly sputum, is often necessary. N-acetyl-1-cysteine and dithiothreitol are liquefying agents in the digestion process and either may be coupled with TB Base Digestant which contains equal volumes of 4% Sodium Hydroxide and 2.9% Sodium Citrate to decontaminate the specimen for complete recovery of mycobacteria.

The GEN-PROBE® AMPLIFIED™ *Mycobacterium tuberculosis* complex (RNA in acid-fast bacilli (AFB) smear positive concentrated sediments prepared from sputum (induced or expectorated), bronchial specimens (e.g., bronchoalveolar lavages or bronchial aspirates) or tracheal aspirates.

The MTD test is to be used as adjunctive test for evaluating AFB smear positive sediments prepared using NACL-NaCH digestion-decontamination of respiratory specimens from untreated patients suspected of having tuberculosis. Patients who have received no antituberculour therapy, less than 7 days of such therapy, or have not received such therapy in the last 12 months may be evaluated with this test. The MTD test should be performed only in laboratories proficient in the culture and identification of *M. tuberculosis* (Level II and Level III or extent 3 and 4). The MTD test should always be performed in conjunction with mycobacterial culture.

The BBL® MGIT *Mycobacteria* Growth Indicator Tube supplemented with BBL® MGIT™ ODAC enrichment and BBL® MGIT™ PANDA™ antibiotic mixture, when appropriate, is intended for the detection and recovery of mycobacteria. Acceptable specimen types are digested and decontaminated clinical specimens (except urine) and sterile body fluids (except blood).

The ACCUPROBE MYCOBACTERIUM GORDONAE CULTURE IDENTIFICATION TEST is a rapid DNA probe test which utilizes the technique of nucleic acid hybridization for the identification of *Mycobacterium gordonae* isolated from culture.

The ACCUPROBE MYCOBACTERIUM AVIUM COMPLEX CULTURE IDENTIFICATION TEST is a rapid DNA probe test which utilizes the technique of nucleic acid hybridization for the identification of *Mycobacterium avium* complex (*M. avium* complex) isolated from culture.

The ACCUPROBE MYCOBACTERIUM TUBERCULOSIS COMPLEX CULTURE IDENTIFICATION TEST is a rapid DNA probe test which utilizes the technique of nucleic acid hybridization for the identification of *Mycobacterium tuberculosis* complex (TB complex) isolated from culture. The TB Complex consists of the following species: *M. tuberculosis, M. bovis, M bovis* BCG, *M. africanum*, and *M. microti* (7).

The ACCUPROBE MYCOBACTERIUM KANSASII CULTURE IDENTIFICATION TEST is a rapid DNA probe test which utilizes the technique of nucleic acid hybridization for the identification of *Mycobacterium kansasii* isolated from culture.

Catalase is an intracellular, soluble enzyme capable of splitting hydrogen peroxide into water and oxygen. The oxygen appears as bubbles in the reaction mixture, indicating catalase activity. All mycobacteria except for some isoniazid-resistant strains of *Mycobacterium tuberculosis* and *Mycobacterium bovis* are catalase positive. However, mycobacteria posses several kinds of catalase that vary in heat stability thus there are two methods of measuring catalase activity.

1. By the relative activity of the enzyme produced by the organism, a semiquantitative test.
2. By the ability of the enzyme to remain active after heating (68° C.), a measure of the heat stability of the enzyme.

Bacto—TB Niacin Test strips are paper strips containing reagents for the detection of niacin production by *Mycobacteria*.

Bacto—TB Niacin Test Control is used as a positive control in the niacin test.

A positive niacin test on a non-chromagenic mycobacteria culture which was isolated from a clinical specimen is strongly indicative of *Mycobacterium tuberculosis*. However, the degree of positivity, i.e. intensity of the reaction depends on the amount of growth present on the slant. A negative reaction with the test culture and a positive reaction with the TB Niacin Test Control disk indicates that the strain tested is not *M. tuberculosis* since niacin negative strains of *M. tuberculosis* are extremely rare, Conversely, a positive niacin test with mycobacteria other than *M. tuberculosis* is also rare since only. *M. simiae* and *M. chelonei* are known to produce niacin.

4.2. Anemia Algorithm

Red blood cell production defects cause anemia that is marked by a low absolute reticulocyte count or a low reticulocyte index. Examination of the peripheral blood count and the bone marrow aids in classifying these disorders.

Production defects associated with apparently normal bone marrow include anemia of chronic disease, e.g. secondary to cancer, infections and inflammatory diseases and other chronic illnesses including liver disorders, congestive heart failure and diabetes mellitus. Production defects associated with marrow aplasia or replacement include aplastic anemia and acquired pure red cell aplasia. Productive defects associated with marrow erythroid hyperplasia and ineffective erythropoiesis include melagoblastic anemias caused by cobalamin or folic acid deficiency, by drugs that interfere with the synthesis of DNA or with the absorption or metabolism of cobalamin and by genetic disorders that interfere with DNA metabolism or with the absorption or distribution of cobalamin.

Figure 2:
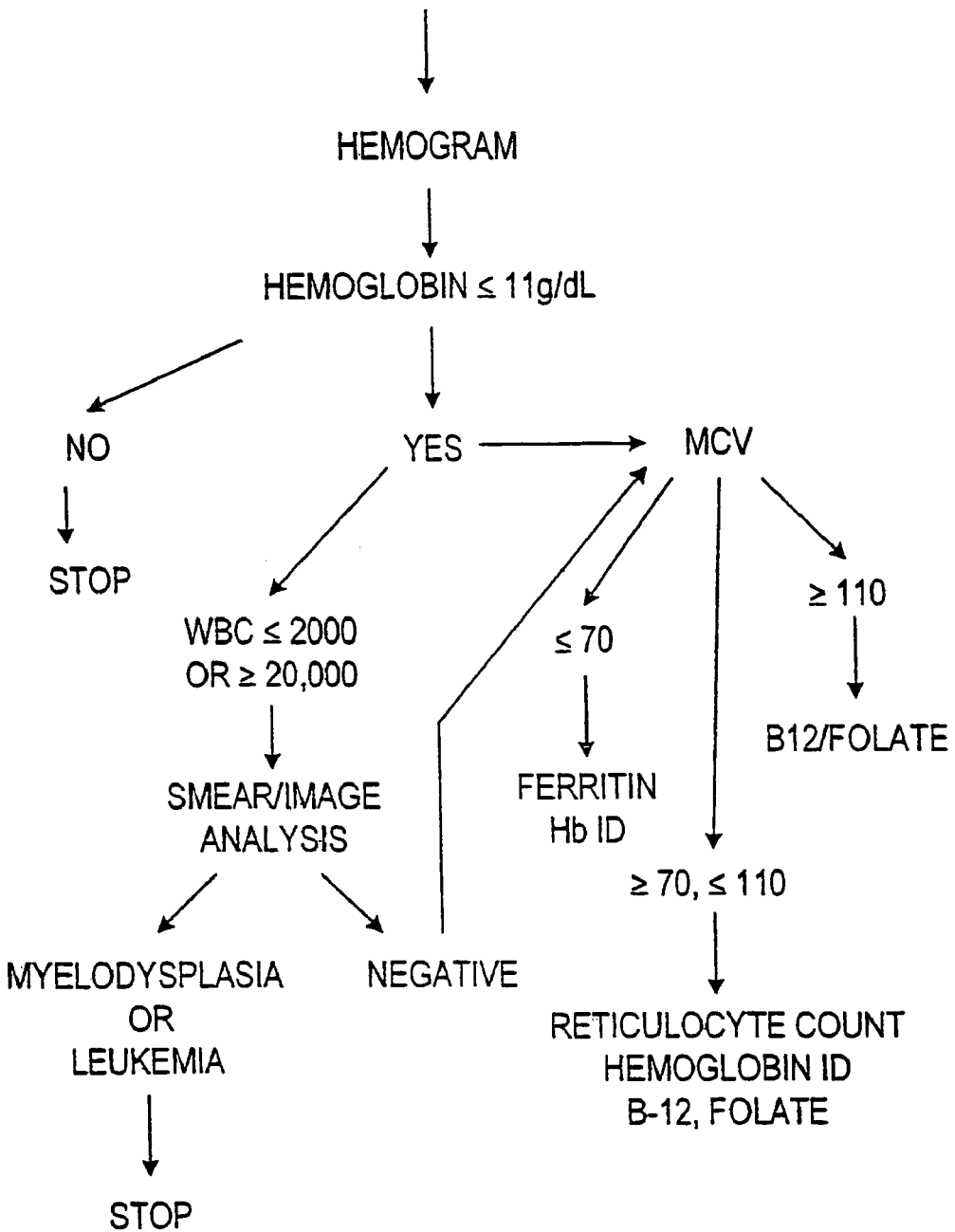
FIG. 2 is a diagram illustrating the anemia algorithm with the follow-up (n+1)st test dependent on the result of the nth assay; the anemia algorithm comprises the steps of a hemogram, hemoglobin, MCV, WBC, B 12, folate, ferritin and reticulocyte count measurements.

FIG. 2 of the present invention describes the anemia algorithm.

Attempting to define an etiology for anemia is one of the more common problems in clinical medicine. The algorithm of the present invention attempts to cover the main causes of anemia in the minimum number of tests.

When an anemia (low hemoglobin concentration) is detected, the algorithm works off of two parameters [white blood cell count (WBC) and mean erythrocyte corpuscular volume (MCV)] in deciding what steps are required. These parameters can be generated by several commercially available instruments (Coulter, Abbott, Bayer). Although slides (smears) of white blood cells are usually done manually, the possibility of automation through image analysis is possible and has been realized at in the present invention through the use of the Micro-21 system.

Current approaches use either an anemia panel in which a large number of tests are ordered on every patient with anemia or the patient is called back to the physician's office on several occasions as the clinician works through a sequence of tests.

It should be noted that the specific numbers for hemoglobin concentration, MCV, and WBC will probably be laboratory specific and depend on the reference ranges defined for the specific population served by that laboratory.

The MICRO21™ is an automated microscopic devise intended for use in locating and displaying specified elements in a medical sample. It has the capability of enhancing the speed, accuracy and consistency with which qualified laboratory personnel can perform laboratory procedures. The operator is able to load, start and walk away while the MICRO21 performs the search process, eliminating much of the fatigue and strain caused by viewing slides through a conventional microscope. With the MICRO21, the qualified operator needs only to return to review the results of the process. All functions of the MICRO21 microscope (slide loading/unloading, focusing, oiling, objective changing and platform movement) are computer-controlled. The MICRO21 acquires images using a color video camera (affixed to the top of the microscope), stores the digitized images on a disk and displays the stored images for review. It then provides various reports summarizing the data.

The MICRO21 system utilizes Neuralvision®, IMI's proprietary use of neural networking and image processing technologies. NeuralVision is a type of artificial intelligence that has the ability to identify specific microscopic objects. It uses capabilities similar to those humans use to recognize faces, cells or other complex objects. The MICRO21 system was NeuralVision to analyze the features of the subject matter: color, shape, size, texture and density, just as technologist would.

MICRO21 processes samples in much the same way as a technologist would, except that much of the work is automated. After samples are prepared, they are processed and the data is associated with the sample record by MICRO21.

Procedures available on MICRO21 loaded with v.4.0 software include:
WBC Differential 50-Cell Differentials
  50 Cells
  Platelet estimates
  WBC Inclusions
  RBC Morphology
WBC Differential 100-Cell Differentials
  50 Cells
  Platelet estimates
  WBC Inclusions
  RBC Morphology
WBC Differential 200-Cell Differentials
  50 Cells
  Platelet estimates
  WBC Inclusions
  RBC Morphology
RBC Morphology
  Platelet Estimates
  RBC Morphology
Reticulocyte Count
CSF Differential For the quantitative determination of ferritin in serum using the Chiron diagnostics ACS.180® Automated Chemiluminescence Systems; to aid in the diagnosis of iron deficiency anemia and iron overload.

The Chiron Diagnostics ACS:180 Ferritin assay is a two-site sandwich immunoassay using direct, chemluminometric technology, which uses constant amounts of two anti-ferritin antibodies. The first antibody, in the Lite Reagent, is polyclonal goal anti-ferritin antibody labeled with acridinium ester. The second antibody, in the Solid Phase, is a monoclonal mouse anti-ferritin antibody, which is covalently coupled to paramagnetic parties.

Detection of hemoglobin variants is important as a diagnostic tool and for genetic counseling, Detecting hemoglobins S, C and E is particularly important because each of these variants in their homozygous state produces clinically significant effects. Additionally, these variants are found as double heterozygotes (Hb, SC, Hb SE) that also produce disease states. Hemoglobin electrophoresis has also become a valuable tool to monitor the percentage of Hb S in patients who have sickle cell anemia and whose therapy includes receiving transfusions. Early treatment of sickle cell anemia (Hb SS) with antibiotics has lessened the infections associated with the disease.

Isoelectric focusing (IEF) takes place in a pH gradient and can only be used for amphoteric substances such as peptides and proteins. The molecules move towards the anode or the cathode until they reach a position in the pH gradient where their net charge is zero. The pH value is the "isoeletric point" (p1) of the substance. Since it is no longer charged, the electric field does not have any influence on it. Should the substance move away-because of diffusion—it will gain a net charge again and the applied electric field will cause it to migrate back to its pI. It is this concentrating effect which leads to the name focusing.

The preparation and separation of hemoglobin is accomplished through the application of a hemoglobin sample onto a precast agarose gel containing RESOLVE ampholytes pH 6–8. RESOLVE ampholytes are composed of low molecular weight amphoteric molecules with varying isoelectric points. When an electrical current is applied to the gel, these molecules migrate through the gel to their isoelectric points (pIs_along the gel, forming a stable pH gradient.

The hemoglobin variants also migrate through the gel until they reach the area where their individual pIs equal the corresponding pH on the gel. At this point, the charges on the variants are zero and migration ceases. The electric filed counteracts diffusion and the hemoglobin variant forms a discrete thin band. When all hemoglobin bands have focused, the gel is fixed in trichloracetic acid. Interpretation of the bands can be done visually or by an imaging Densitometer.

For the quantitative determination of folate in serum or red blood cells Chiron Diagnostics ACS:180® Automated Chemiluminescence Systems are used.

Low folate intake, malabsorportion as a result of gastrointestinal diseases, pregnancy, and drugs such as phenyloin are causes of folate deficiency. Folate deficiency is also associated with chronic alcoholism. Folate and vitamin $B_{12}$ deficiency impair DNA synthesis, causing macrocytic anemias. These anemias are characterized by abnormal maturation of red blood cell precursors in the bone marrow, the presence of megaloblasts, and decreased red blood cell survival.

Since both folate and vitamin $B_{12}$ deficiency can cause macrocytic anemia, appropriate treatment depends on the differential diagnosis of the deficiency. Serum folate measurement provides an early index of folate status. However, folate is much more concentrated in red blood cells than in serum so the red blood cell folate measurement more closely reflects tissue stores. Red blood cell folate concentration is considered the most reliable indicator of folate status.

The Chiron Diagnostics ACS:180 Folate assay is a competitive immunoassay using direct, chemiluminescent technology. Folate in the patient sample competes with acridinium ester labeled folate in the Lite Reagant for a limited amount of folate binding protein, which is covalently coupled to paramagnetic particles in the Solid Phase. The ACS:180 Folate assay uses Releasing Agent (sodium hydroxide) and DTT to release the folate from endogenous binding proteins in the sample.

For the quantitative determination of vitamin $B_{12}$ in serum or plasma Chiron diagnostics ACS:180 Automated Chemiluminescence Systems is used.

Clinical and laboratory findings for $B_{12}$ deficiency include neurological abnormalities, decreased serum $B_{12}$ levels, and increased excretion of methylmaloric acid. The impaired DNA synthesis associated with vitamin $B_{12}$ deficiency causes macrocylic anemias. These anemias are characterized by abnormal maturation of erythrocyte precursors in the bone marrow, which results in the presence of megaloblasts and in decreased erythrocyte survival.

Pernicious anemia is a macrocytic anemia caused by vitamin $B_{12}$ deficiency that is due to lack of intrinsic labor. Low vitamin $B_{12}$ intake, gastrectomy, diseases of the small intestine, malabsorption and trans-cobalamin deficiency can also cause vitamin $B_{12}$ deficiency.

The Chiron Diagnostics ACS:180 VB12 assay is a competitive assay in which vitamin $B_{12}$ from the patent sample competes with vitamin $B_{12}$ labeled with acridinium ester in the Lite Reagent, for a limited amount of purified intrinsic factor, which is covalently coupled to paramagnetic particles in the Solid Phase. The assay uses Releasing Agent (sodium hydroxide) and DTT to release the vitamin $B_{12}$ from endogenous binding proteins in the sample and cobinamide to prevent rebinding after the Solid Phase is added to the sample.

4.3. Cardiac Risk Algorithm

Despite the recent reduction in deaths due to myocardial infarction, approximately 1.5 million people in the United States suffer acute myocardial infarction each year, and 500,000 due. Some of the factors responsible for the sudden thrombolic occlusion of a coronary artery include the formation of atherosclerotic plaques rich in foam cells or lipid-laden macrophages. These plaques are susceptible to sudden rupture and hemorrhage into the vessel wall which may result in the sudden partial or total occlusion of the coronary artery (McGovern, P G et al., 1996, N. Eng. J. Med. 334, 884).

Figure 3:
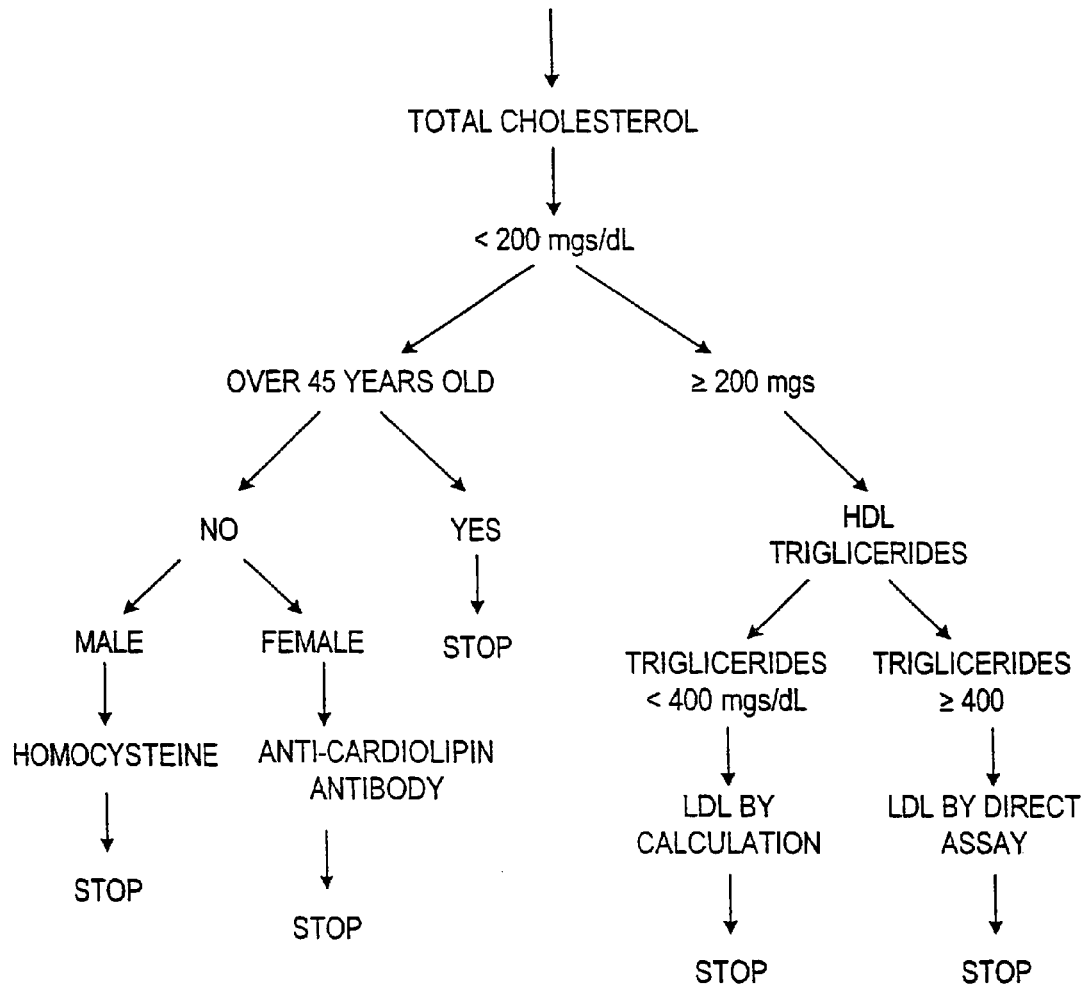
FIG. 3 is a diagram illustrating the cardiac algorithm with the follow-up (n+1)st test dependent on the result of the nth assay; the cardiac algorithm comprises the steps of measuring total cholesterol, homocysteine, HDL triglycerides and LDL.

The basic components of the approach to the cardiac patient are history, physical examination, and laboratory studies such as chest x-ray, electrocardiogram, and blood lipid profiles. A number of more specialized procedures such as a Doppler echocardiographic study can enable the physician to make a precise cardiovascular diagnosis. However, specialized diagnostic tests are usually expensive and some entail significant risk for the patient. Therefore, laboratory examination has frequently replaced observation in clinical practice. For example, FIG. 3 of the present invention describes the algorithm for cardiac risk.

Atheroscelerotic cardiovascular disease (ASCVD) resulting in acute myocardial infarction, stroke and peripheral vascular disease is a major cause of morbidity and mortality in the United States and other affluent industrialized countries.

Currently assessment of risk for ASCVD is generally done using a panel of lipid assays with low density lipoprotein cholesterol (LDL-C) is calculated using the Freidwald equation. The latter strategy is appropriate if the triglyceride concentration is <400 mgs/dL. If the triglyceride concentration is however ≧400 mgs/dL than the equation is not applicable. The CLS algorithm, utilizing the recommendations of the National Cholesterol Education Project (NCEP) eliminates un-necessary lipid testing on los risk individuals (total cholesterol<200 mgs/dL). Also, it provides for automatic reflexing to a direct assay for LDL/C when the triglyceride concentration is ≧400 mgs/dL.

Finally, the CLS algorithm takes note of the problem of atherosclerotic vascular disease in young adults with normal lipid parameters by investigating accessible risk factors for arterial thrombosis (C-Reactive Protein, and homocysteine) in such individuals. In the event of elevated CRP or homocysteine an assay for D-Dimer is performed. D-Dimer is a global test for activation of the coagulation pathway and may suggest a subgroup of patients at particularly high risk for thrombosis. Depending on the availability of suitable reagents substitution of prothrombin fragment F1.2 for D-dimer may improve the algorithm (S. Agewall et al, *J. Hypertension* 16:1555 (1998). Research will undoubtedly continue to reveal additional risk factors for ASCVD and depending on their relative frequency and importance they can be readily incorporated into the framework of the algorithm.

This algorithm provides data on chemical risk factors which the physician can combine with clinical risk factors such as hypertension and cigarette smoking to obtain an overall portrait of cardiovascular risk in a highly efficient manner.

Total cholesterol in serum comprises all of the cholesterol found in various lipoproteins. Cholesterol is the major component of the low density lipoprotein (LDL) fraction, and a minor component of the very low density lipoprotein (VLDL) and high density lipoprotein (HDL) fractions. Elevated LDL has consistently been associated with incidence of atherosclerosis. There is also a strong correlation between considerably elevated serum cholesterol levels and an increase tendency for atherosclerosis. However, HDL cholesterol concentration and cardiovascular disease risk are inversely related. Hence, the concentration of cholesterol associated wit HDL fraction of lipoproteins also shows an inverse relationship with cardiovascular disease. Measurement of total and HDL cholesterol in serum is useful in evaluating cardiovascular disease. Measurement of total and HDL cholesterol in serum is useful in evaluating cardiovascular disease risk. Cholesterol measurements are also important in the diagnosis and management of numerous other diseases.

Plasma lipoproteins are spherical particles containing varying amounts of cholesterol, triglycerides, phospholipids and proteins. The phospholipid, free cholesterol and protein constitute the outer surface of the lipoprotein particle, while the inner core contains mostly esterified cholesterol and triglyceride. These particles serve to solubilize and transport cholesterol and triglyceride in the bloodstream.

The relative proportions of protein and lipid determine the density of these lipoproteins and provide a basis on which to begin their classification. These classes are: chylomicron, very-low-density lipoprotein (VLDL), low-density lipoprotein (LDL) and high-density liproprotein (HDL). Numerous clinical studies have shown that the different lipoprotein classes have very distinct and varied effects on coronary heart disease risk.

The principle role of HDL in lipid metabolism is the uptake and transport of cholesterol from peripheral tissues to the liver through a process known as reverse cholesterol transport (a proposed cardioprotective mechanism). Low HDL levels are associated with an increased risk of coronary heart disease and coronary artery disease. Hence, the determination of serum HDL is a useful tool in identifying high-risk patients. The Adult Treatment Panel of the national Cholesterol Education Program (NCEP) recommends that all adults 20 years of age and over should have their total cholesterol and HDL cholesterol levels measured at least every 5 years to screen for coronary heart disease risk.

The Liquid Select HDL Cholesterol assay is a homogeneous method for directly measuring serum HDL-C levels in serum or plasma without the need for any off-line pretreatment or centrifugation steps.

The method is in a two reagent format and depends on the properties of a unique detergent, as illustrated below. This detergent solubilizes only the HDL lipoprotein particles, thus releasing HDL cholesterol to react with cholesterol to produce color. In addition to selectively disrupting the HDL lipoprotein particles, this unique detergent also inhibits the reaction of the cholesterol enzymes with LDL, VLDL and chylomicron lipoproteins by absorbing to their surfaces. A polyanion is contained in the first reagent to assist with complexing LDL, VLDL and chylomicron lipoproteins, further enhancing the selectivity of the detergent and enzymes for HDL cholesterol.

The IMx Homocysteine assay is a Fluorescence Polarization Immunoassay (FPIA) for the quantitative measurement of total L-homocysteine in human serum or plasma on the IMx Analyzer. The device can assist in the diagnosis and treatment of patients suspected of having hyperhomocysteinemia and homocystinuria.

Figure 4:
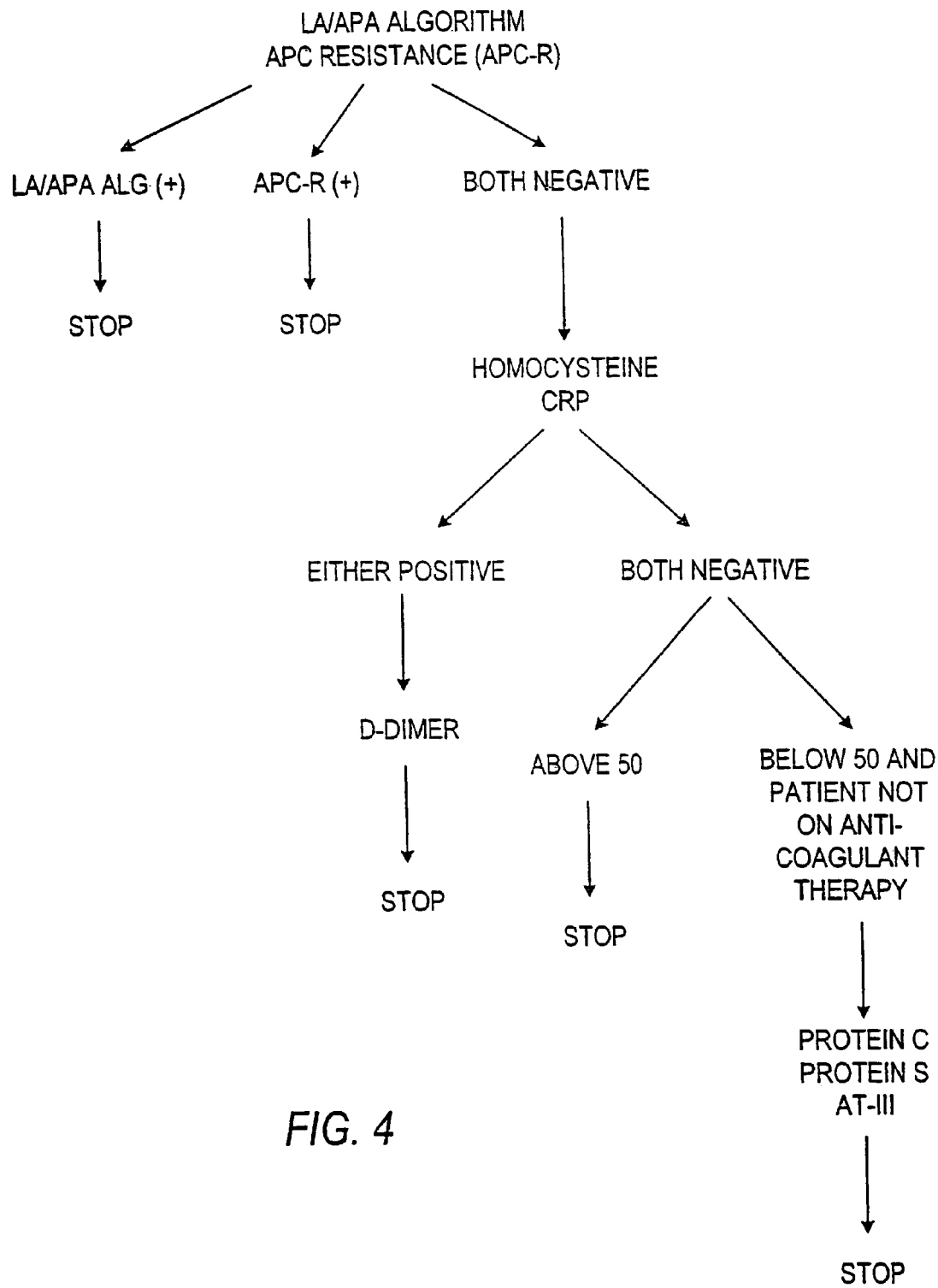
FIG. 4 describes the thrombophilia algorithm with the follow-up (n+1)st test dependent on the result of the nth assay.

The thrombophilia algorithm applies to thrombosis and pulmonary embolism and is described in FIG. 4.

Deep venous thrombosis and pulmonary embolus are major health problem in the United States and Europe. An etiology cannot currently be established in ca. 50 percent of cases. Being able to establish a diagnosis however, can be important because several entities have a genetic character [e.g. activated protein C resistance (APC-R), hereditary protein C, S. and anti-thrombin III deficiencies] and diagnosis carries implications for screening family members.

The proposed algorithm uses reagents and techniques accessible to the routine chemistry laboratory. Patients with direct evidence of thrombophilia (e.g. a history of deep venous thrombosis) and completely negative results on the suggested algorithm would require evaluation in a research setting. Although the basic concept of a thrombophilia algorithm would not be invalidated the latter approach may require amendment as new research results become translated into new laboratory tests.

The most common known causes of thrombophilia are APC-R and Lupus anticoagulant/anti-phospholipid antibody. These assays therefore lead the algorithm. If both are negative (detection of LAC/APA itself involves an algorithm whose design has been separately submitted) then homocysteine and C-reactive protein (CRP) are assayed. Hyperhomocysteinemia has been associated with thrombotic tendencies while CRP is a marker of inflammation and possible endothelial cell damage (H. Refsum et al, *Annu. Rev. Medicine,* 49:31 (1998) and P. M. Ridker et al, *Circulation* 98:731 (1998)). D-Dimer is a "global" marker of fibrin formation (and therefore thrombin formation). In conjunction with an increased CRP or homocysteine an elevated D-Dimer could point to a subpopulation of patients with enhanced thrombotic risk. Depending on the availability of suitable reagents evaluation of F1.2 as a replacement for D-Dimer may be merited (S. Agewall et al, *J. Hypertension* 16:1555 (1998)). This however, represents an amendment of the algorithm rather than an invalidation of the concept.

If the patient is not on anti-coagulant therapy (information to be provided on the requisition) then further evaluation for the rather rare deficiencies of Protein C, Protein S and anti-thrombin III would be justified, if all earlier assays in the algorithm are negative.

It should be noted that as a result of differences in gene frequencies among ethnic and racial groups, adaptation of this algorithm may be required in different geographical locations. The basic concept of a thrombophilia algorithm however, is not invalidated by this situation.

4.4. HBs Ag Algorithm

Viral hepatitis is primarily a disease of the liver that is caused by a number of viruses, including hepatitis B virus (HBV) and HDV.

Hepatitis B is transmitted by percutaneous exposure to blood, blood products, and blood contaminated instruments. Intimate contact, especially sexual contact, and perinatal spread from mother to newborn are the two other modes of HBV transmission.

Ultrastructural examination of particles observed in sera of patients with HBV infection reveals three entities. the terminology used to describe the various antigens and antibodies associated with HBV is given below:

TABLE 1

| Term | Abbreviation | Description |
| --- | --- | --- |
| Hepatitis B virus | HBV | 42-nm-diam double-shelled particle that consists of 7-nm-diam outer shell and 27-nm-diam inner core. Core contains small, circular, partially double-stranded DNA molecule and DNA polymerase activity. Originally called the Dane particle. This is the |

TABLE 1-continued

| Term | Abbreviation | Description |
| --- | --- | --- |
| | | prototype for family Hepadnaviridae. |
| Hepatitis B surface antigen | HBsAg | Complex antigen found on surface of HBV and on 20-nm-diam particles and tubular forms. Formerly designated Australia (Au) antigen or hepatitis-associated antigen. |
| Hepatitis B core antigen | HBcAg | Antigen associated with 27-nm-diam core of HBV. |
| Hepatitis B e antigen | HBeAg | Antigen closely associated with nucleocapsid of HBV. Also found as soluble protein in serum. |
| Antibodies to HBsAg, HBcAg, and HBeAg | Anti-HBs, anti-HBc, and anti-HBe, respectively | Specific antibodies produced in response to their respective antigens |

A number of serologic techniques with different degrees of sensitivity and specificity have been developed for the detection of HBV antigens and their specific antibodies:

TABLE 2

| | Manufacturer[a] | |
| --- | --- | --- |
| Assay | RIA | EIA |
| HBsAg | 1, 5 | 1, 2, 3, 4, 5[b] |
| Anti-HBs | 1, 5 | 1, 5[b] |
| Anti-HBc | 1, 5 | 1, 4, 5 |
| IgM Anti-HBc | 1, 5 | 1, 5 |
| HBeAg/Anti-HBe | 1, 5 | 1, 5 |
| HBV DNA | 1 | |

[a]1, Abbott Laboratories; 2, Genetic Systems Corp.; 3, Organon Teknika Corp.; 4, Ortho Diagnostic Systems; 5, Sorin/Incstar Corp.
[b]Unlicensed assay; for research only; not for use in diagnostic procedures.

Successful detection of HBV serologic markers depends on the relative sensitivity of the test procedures and on the availability of personnel who can understand the procedures and are meticulous in the performance of the test.

Figure 5:
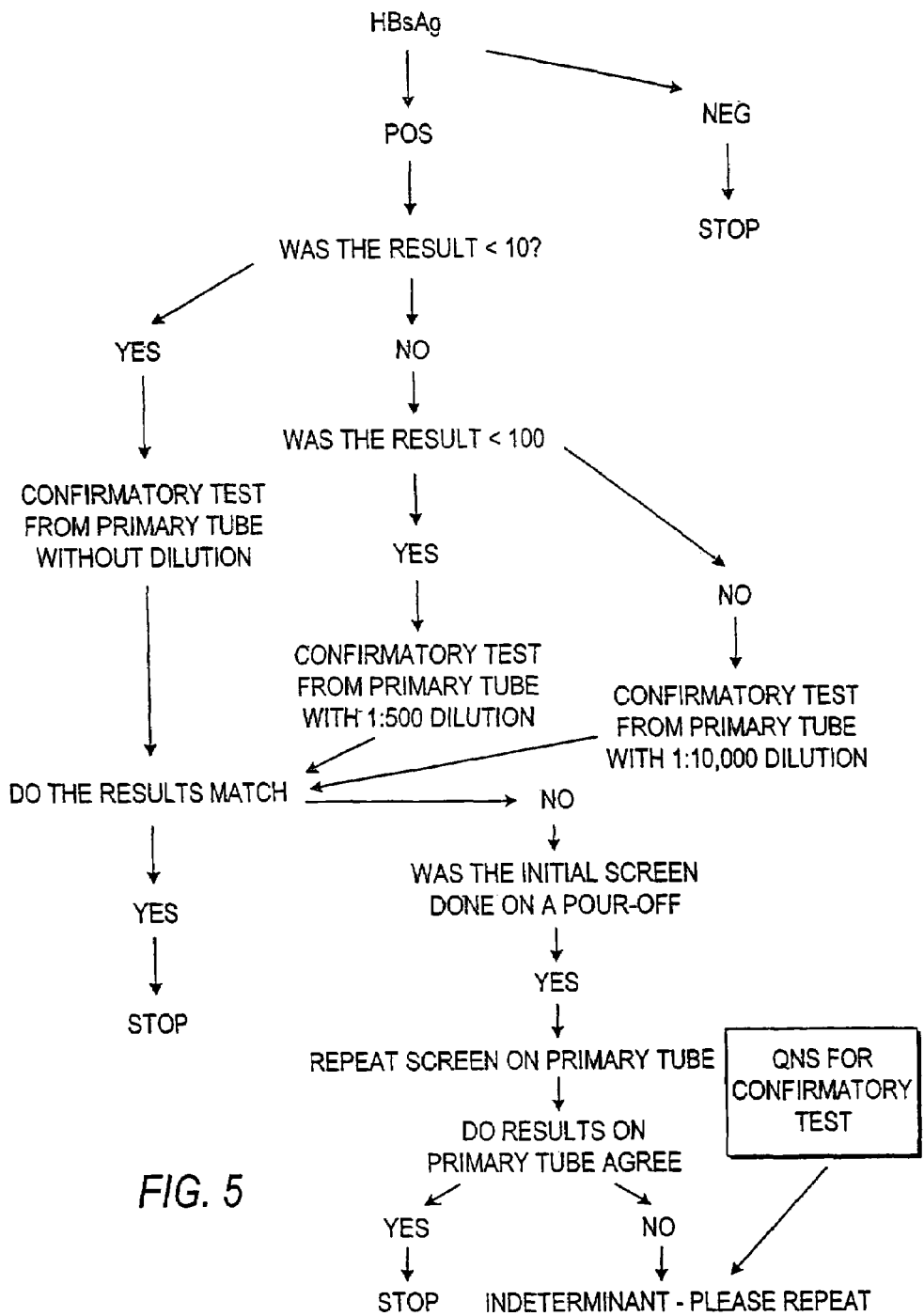
FIG. 5 is a diagram illustrating the HBsAg algorithm for prenatal and dialysis specimen with the follow-up (n+1)st test dependent on the result of the nth assay; the algorithm measures hepatitis B.

FIG. 5 describes the algorithm for chronic Hepatitis B which results from vertical transmission during birth.

Chronic Hepatitis B, frequently resulting from vertical (mother-child) transmission at the time of pass age through the birth canal is an important public health problem.

The monitoring algorithm is designed for two discrete population groups:

1. Children born to Hepatitis B carrier mothers who must be evaluated to determined disease status.
2. Patients with known chronic Hepatitis who need to be followed periodically pre and post therapy.

The notation is identical to that noted in the diagnostic algorithm. That algorithm provided baseline SGPT (ALT) and AFP measurements. Viral Load measurements are provided in Hbe antigen positive cases in which viral loads are generally higher and hence amenable to measurement with technology available to the routine clinical lab (K. Fujinara et al *Dig. Dis. Sci.* 43:368 (1998)). As new technology becomes available (K. Kamisango et al, *J. Clin. Micro.* 37:310 (1999)) the algorithm may be improved with the ability to use BBV viral load assays in Hbe Ab positive carriers.

The assays for HBsAG are routinely used to diagnose suspected HBV infection and to monitor the status of infected individuals; i.e., whether the patient has resolved infection or has become a chronic carrier of the virus. The efficacy of anti-viral drugs also have been evaluated by measuring the levels of HBsAg in patient sera or plasma. The Centers for Disease Control and Prevention have recommended the prenatal screening of all pregnant women so that newborns from HBV carrier mothers may obtain prophylactic treatment. Prenatal transmission of HBV infection from mother to neonate is the major mode of transmission in an HBV endemic population.

Specimens nonreactive by IMx HBsAg are considered negative for HBsAg. A reactive specimen must be retested in duplicate by the IMx HBsAg test to determine whether it is repeatedly reactive. A specimen which is found to be repeatedly reactive must be confirmed by licensed neutralization procedures utilizing human anti-HBs (IMx HBsAg Confirmatory Assay). If the specimen is neutralizable in the confirmatory test, the specimen is considered positive for HBsAg.

Hepatitis B e Antigen (HBeAG) Assay

The ABBOTT HBe (rDNA) EIA test uses the "sandwich principle," a solid phase enzyme immunoassay technique, to measure HBeAg levels in serum and plasma. Beads coated with human anti-HBe are incubated with serum or plasma specimens. Hepatitis B antigen, if present in the specimen, is immunologically coupled to the antibody coated bead. During a second incubation, antibody conjugated with horseradish peroxidase is bound to any HBeAg on the bead creating an antibody-antigen-antibody "sandwich." Within limits, the greater the amount of antigen in the specimen, the higher the absorbance.

Unbound enzyme conjugate is then removed and the beads washed. Next o-Phenylenediamine (OPD) solution containing hydrogen peroxide is added to the bead and, after incubation, a yellow color develops in proportion to the amount of HBeAg which is bound to the bead. The enzyme reaction is stopped by the addition of acid.

The absorbance of controls and specimens is determined using a spetrophotometer with wavelength set at 492 nonometers (nm). Specimens giving absorbance values equal to or greater than the Cutoff value (the absorbance value of the Negative Control Mean plus a factor of 0.06) are considered reactive for HBeAg. Specimens which are repeatedly reactive by this assay are considered positive for the presence of NBeAg by the criteria of the ABBOTT HBe(rDNA) EIA test. Specimens with absorbance values less than the Cutoff Value of considered negative for HBeAg.

Antibody to Hepatitis B e Antigen (Anti-HBe) Assay

The ABBOTT HBe (rDNA) EIA test for anti-HBe is based upon the principle of competitive binding between anti-HBe in the test specimen and Antibody to Hepatitis B e Antigen (Human) Coated Beads for a standardized amount of recombinant DNA hepatitis B e antigen (rDNA HBeAg), the Neutralizing Reagent.

An anti-HBe Coated Bead is incubated with the Neutralizing Reagent and the specimen. If anti-HBe is present in the specimen, it will compete with anti-HBe bound to the coated bead for rDNA HBeAg present in the Neutralizing Reagent. Thus, the amount of rDNA HBeAg immunoligically coupled to the bead will progressively decrease as the concentration of anti-HBe in the specimen increases. After removing unbound reactants, a second incubation is performed with antibody conjugated with horseradish perixidase (anti-HBe: HHRPO). If anti-HBe was present in the specimen, less rDNA HBeAg would be coupled to the bead and therefore less anti-HBe:HHRPO would bind to the bead for completion of the "sandwich." Within limits, the greater the amount of the anti-HBe in the specimen, the lower the absorbance.

The absorbance of the specimen is compared to the Cutoff Value which is one-half of the sum of the absorbance values of the Negative Control mean plus Positive Control mean. Specimens with absorbance values equal to or less than the Cutoff Value are considered reactive for anti-HBe by the criteria of the ABBOTT HBe (rDNA) EIA Test. Specimens with absorbance values greater than the Cutoff Value are considered negative for anti-HBe.

All ACS assays utilize paramagnetic particles as the solid phase, and acridinium ester as the chemiluminescent label. AC S AFP is a two-site chemiluminometric (sandwich) immunoassay which uses a constant amount of two antibodies. The first antibody or Lite Reagent is an affinity purified polyclonal rabbit anti-AFP antibody labeled with acridinium ester. The second antibody or solid phase is a monoclonal mouse anti-AFP antibody covalently coupled to paramagnetic particles.

The ACS AFP assay is standardized against the World Health Organization International Reference Preparation 72/225 using highly purified AFP. The results are reported in ng/mL for serum AFP and in ug/mL for amniotic fluid AFP.

AFP is a single chain glycoprotein with a molecular weight of approximately 70,000 daltons. AFP was first described as a fetal protein by Bergstrand and Czar in 1956. AFP and albumin share considerable sequence homology and some physiological functions. Fetal AFP synthesis occurs in the liver, yolk sac, and gastrointestinal tract. AFP produced by the fetus is secreted into fetal serum, reaches a peak at 13 weeks gestation, and then gradually declines during gestation. Shortly after birth, the newborn's AFP level reaches the normal adult level. In adults, serum AFP concentrations remain low except during pregnancy, benign liver diseases (hepatitis, cirrhosis), primary hepatocellular carcinoma, and certain germ cell tumors.

During pregnancy, maternal serum AFP (MSAFP) levels rise through the third trimester. Elevated or depressed AFP levels may indicate fetal problems. Elevated MSAFP levels during the second trimester of pregnancy are often associated with one of the most common types of birth defects, open neural tube defects (NTDs). A number of studies have confirmed the utility of AFP testing to detect NTDs during the second trimester of pregnancy.

In addition to AFP testing, maternal factors such as race, weight, age, diabetes, and family history must be considered when assessing the open NTD risk. Final determination of open NTD depends on information provided by confirmatory testing since conditions other than open NTDS, such as cirrhosis, hepatitis, certain types of cancer, and other fetal malformations (ventral wall defects, defective kidneys, and others), may also cause elevated MSAFP levels. Such testing includes amniotic fluid AFP (AFAFP), acetylcholinesterase, amniography, and ultrasonography. Depressed MSAFP levels have been reported in other conditions.

The enzyme ALT (alanine aminotrasferese) has been found to be in highest concentration in the liver, with decreasing concentrations found in kidney, heart, skeletal muscles, pancreas, spleen and lung tissue respectively. ALT measurements are used in the diagnosis and treatment of certain liver disease (eg. viral hepatitis and cirrhosis) and heart diseases.

The QUANTIPLEX™ HBV DNA Assay (bDNA) is a sandwich nucleic-acid hybridization procedure for the quantification of hepatitis B virus (HBV) DNA in human serum (see FIG. 1.) After HBV genomic DNA is released from the virions, its capture to an HBV Capture Well is mediated by a set of specific synthetic oligonucleotide target probes. A second set of target probes hybridizes to the viral DNA and branched DNA (bDNA) amplifiers. The two sets of target probes bind to specific sequences on the minus-sense strand of the viral DNA. Multiple copies of an alkaline-phosphatase-conjugated probe are then hybridized to this immobilized complex to amplify the signal. Detection is achieved by incubating the complex with a chemiluminescent substrate and measuring the light emission generated by the bound alkaline phosphatase reacting with the chemiluminescent substrate. Light emission is directly proportional to the amount of HBV DNA present in each sample, and results are recorded as luminescent counts by a plate luminometer. A standard curve is defined by light emission from standards with known concentrations of HBV DNA. Concentrations of HBV DNA is specimens are determined from this standard curve.

Figure 8:
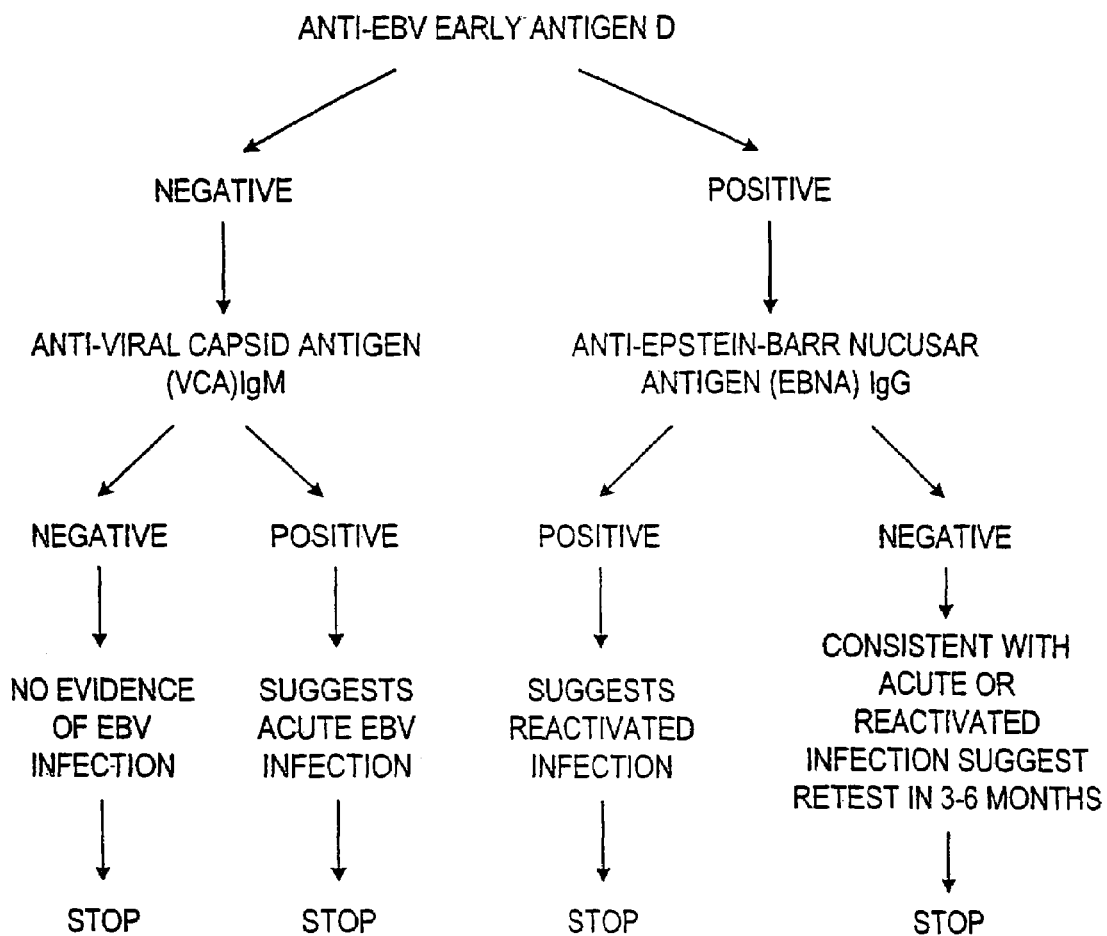
FIG. 8 is a diagram illustrating the Epstein-Barr Virus Algorithm with the follow-up (n+1)st test dependent on the result of the nth assay; the algorithm yields results in cases which are heterophile antibody negative (10–20%) as well as covering those cases which would be heterophile antibody positive; the result obtained with antibody to EBV early antigen D may be negative to indicate that the next step should be the test with antibody to viral capsid antigen. The result may be positive to indicate that the next step should be to test with antibody to E-B nuclear antigen IgG.
Figure 9:
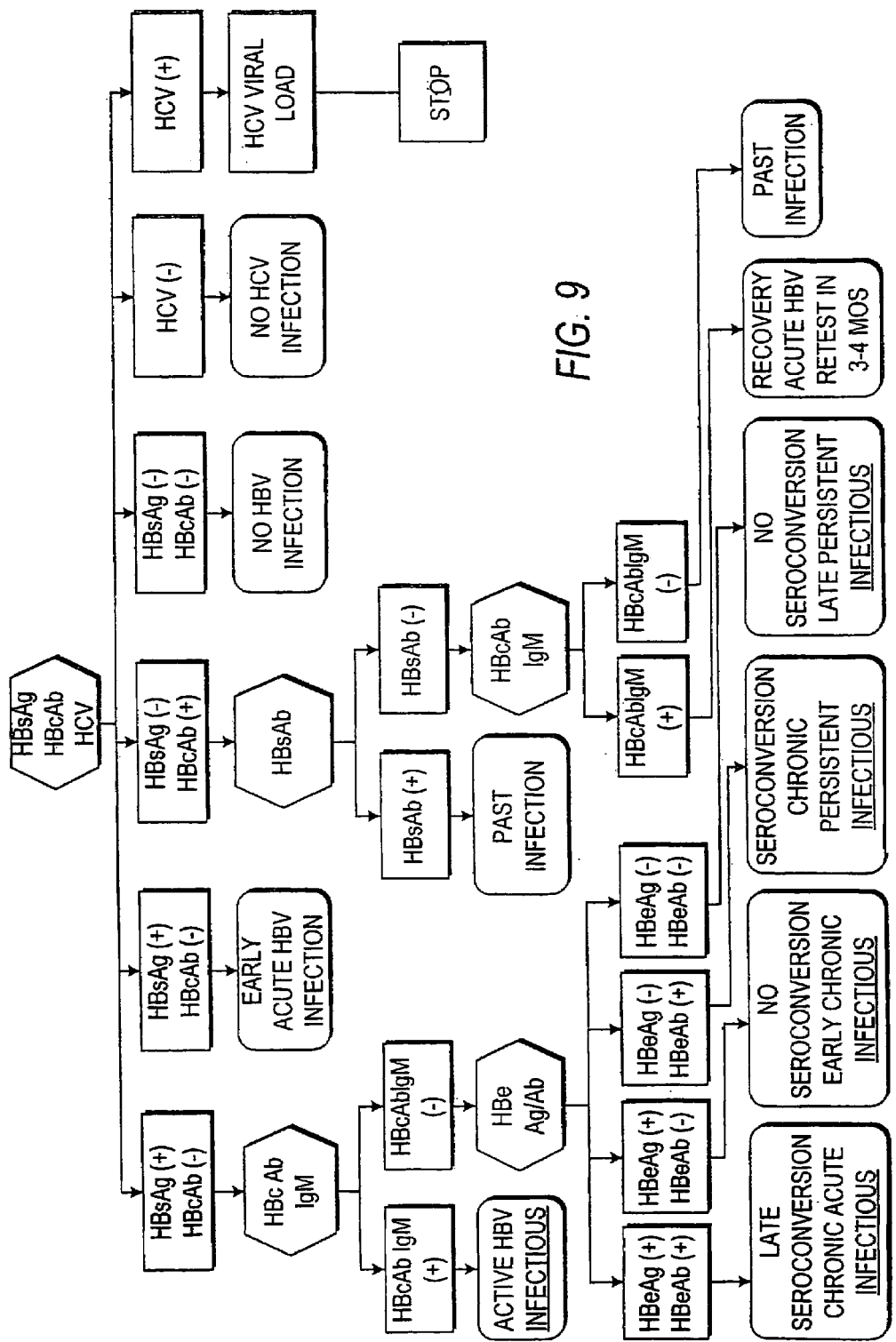
FIG. 9 is a diagram illustrating the Hepatitis algorithm with the follow-up (n+1)st test dependent on the result of the nth assay; the hepatitis algorithm measures HBsAG, HBcAb and HCV.
Figure 14:
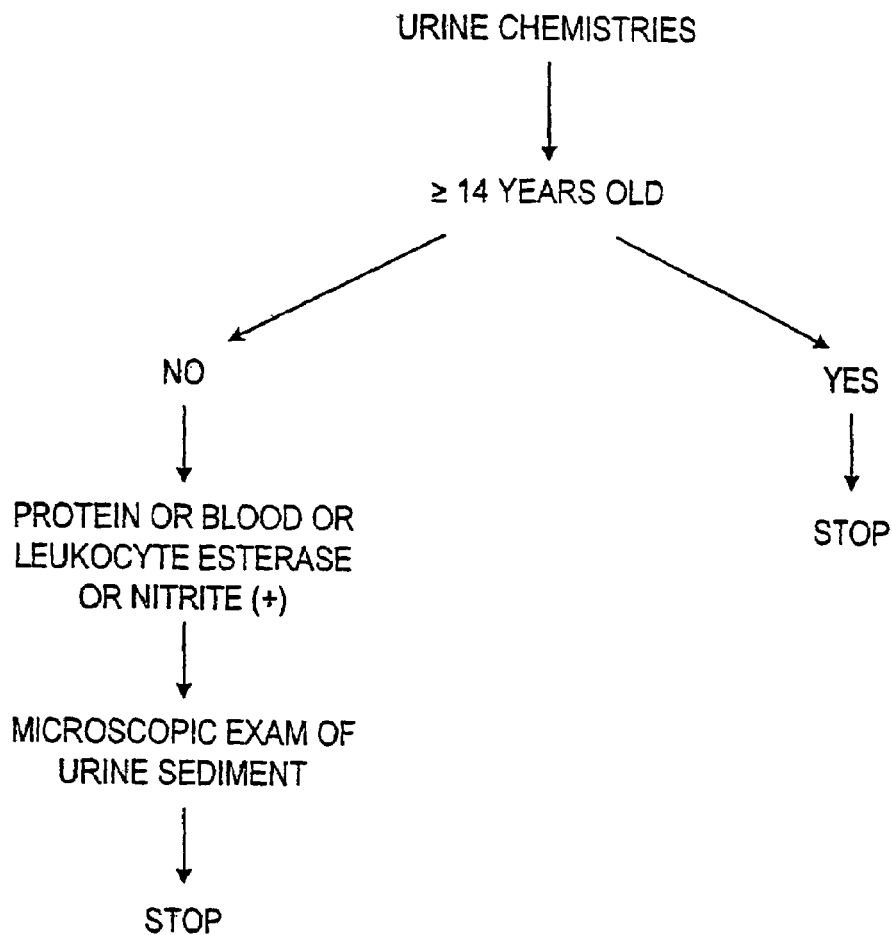
FIG. 14 is a diagram illustrating the urinalysis algorithm with the follow-up (n+1)st test dependent on the result of the nth assay; the algorithm provides for quantitative urine chemistries which in negative samples is further continued to measure protein, blood, leukocyte esterase or nitrite.

FIG. 8 and FIG. 14 also describe the hepatitis diagnostic algorithms in detail.

The association of chronic Hepatitis B and Hepatitis C with liver failure and hepatocellular carcinoma is well known. But there are few diseases which rival Hepatitis B with respect to the number of assays needed to assess infectious/immune status and about which the laboratory gets as many phone calls with respect to interpretation.

The CLS algorithm takes the clinician down defined pathways leading to readily interpretable patterns. In the algorithmic approach, two major advantages, as compared to historical approaches, are that an algorithmic approach reduces costs by avoiding a shot gun approach (all tests on all specimens) and by generating readily interpretable result patterns.

The diagnostic algorithm starts off with assays for the Hepatitis B surface antigen (HbsAg) and antibodies to the Hepatitis B core antigen (HbcAb) and to the Hepatitis C virus (HCV). By adding on assays for the IgM class antibody against Hepatitis B core antigen, antibody against the hepatitis surface antibody, Hbe antigen and anti-Hbe antibody patterns defining the patient's infectious/immune status with respect to BBV and HCV may be generated.

Although HbeAg/HBeAb remains an important indicator of prognosis and response to therapy (K. Fujinara et al, *Dig. Dis. Sci.* 43:368 (1998) the emergence of pre-core mutants which do not make Hbe antigen has created new difficulties with respect to patient assessment (Incident Investigation Team, *N. Engl. J. Med.* 336:178 (1997). Although direct measurement of viral copies might be a solution, current technology available to the typical clinical laboratory is insensitive for this purpose. Methods with higher sensitivity are on the way (K. Kamisango et al, *J. Clin. Micro.* 37:310 (1999)) and a future improvement in the algorithm may involve replacement of HbeAg/Ab measurements with HBV viral load measurements.

For patients who are HCV seropositive, there is some indication that viral load may have prognostic significance and hence is included at the time of diagnosis in order to provide a baseline at diagnosis. Given the association of HBV and HCV with hepatocellular carcinoma, a marker of this disease [alphafetoprotein] (AFP) is also included at time of diagnosis.

For purposes of providing a baseline for subsequent patient monitoring measurement of a standard marker of hepatocellular injury (ALT) is also provided.

IMx HBsAg is a qualitative third generation Microparticle Enzyme Immunoassay for the detection of Hepatitis B Surface Antigen (HBsAg) in human serum or plasma.

AUSAB® EIA is an enzyme immunoassay for the qualitative determination of Antibody to Hepatitis B Surface Antigen (anti-HBs) in serum or plasma.

The AUSAB EIA test for anti-HBs uses the "sandwich principle" a solid phase enzyme-linked immunoassay technique to detect anti-HBs levels in serum or plasma. Polystyrene beads coated with human Hepatitis B Surface Antigen (HBsAg) are incubated with either the patient specimen or the appropriate controls.

The IMx CORE-M assay is a Microparticle Enzyme Immunoassay (MEIA) for the qualitative determination of IgM antibody against Hepatitis B Core Antigen (HBcAg) in human serum or plasma and is indicated for use as an aid in the diagnosis of acute or recent (usually six months or less) hepatitis B viral infection.

The enzyme ALT (alanine aminotransferase) has been found to be in highest concentration in the liver, with decreasing concentrations found in kidney, heart, skeletal muscles, pancreas, spleen and lung tissue respectively. ALT measurements are used in the diagnosis and treatment of certain liver disease (eg. viral hepatitis and cirrhosis) and heart diseases.

The QUANTIPLEX™ HCV RNA 2.0 Assay ((bDNA) is a sandwich nucleic-acid hybridization procedure for the quantification of hepatitis C viral (HCV) RNA in human serum and plasma. After HCV genomic RNA is released from the virions, its capture to a HCV Capture Well is mediated by a set of specific, synthetic oligonucleotide target probes. A second set of target probes hybridizes to the viral RNA and branched DNA (bDNA) amplifiers. The two sets of target probes bind to the 5' untranslated and core regions of the HCV genome. Multiple copies of an alkaline-phosphatase-conjugated probe are then hybridized to this immobilized complex to amplify the signal. Detection is achieved by incubating the complex with a chemiluminescent substrate and measuring the light emission generated by the bound alkaline phosphatase reacting with the chemiluminescent substrate. Light emission is directly proportional to the amount of HCV RNA present in each sample, and results are recorded as luminescent counts by a plate luminometer. A standard curve is defined by light emission from standards with known concentrations of recombinant bacteriophage. Concentrations of HCV RNA is specimens are determined from this standard curve.

4.5. Breast Cancer Algorithm

Projection of the causes of death among humans indicates that by 2000, cancer will be the leading cause of death in the United States. Even in the face of an enormous research effort, the overall mortality rate of cancer has not changed over the last forty years. In 1997 the estimated number of new cancer cases excluding skin is 1.38 million. Prostate cancer is the leader, followed by cancer of the breast, lung, colon-rectum, and bladder.

Cancer is a relatively autonomous growth of tissue. The proliferation of normal cells is thought to be regulated by growth promoting oncogenes and counter balanced growth constraining tumor suppressor genes. Early detection of cancer offers the best chance for cure. In general, tumor markers may be used for diagnosis, prognosis and monitoring effects of therapy and for targets for localization and therapy. Ideally, tumor marker should be produced by the tumor cells and be detectable in body fluids. It should not be present in healthy people or in benign conditions. However, most tumor markers are present in normal, benign, and cancer tissues and are not specific enough for screening cancer.

Breast cancer is the most common form of malignant disease in women in western countries; in the United States, it is the most common cause of death in women between 40 and 55 years of age. This disease will develop in about 12 percent of women in the United States. About 70 percent of this group can be cured.

Most tumor marker values correlate with the effectiveness of treatment and responses to therapy. In breast cancer, the concentration of markers such as CA 549 changes with the treatment and clinical outcome of the patient. The CA 549 marker may be used to determine the success of the initial treatment (e.g. surgery or radiation), detect the recurrence of breast cancer and monitor the effectiveness of the treatment modality (Chan D W et al., 1988, Clin. Chem. 34; 2000–2004).

Figure 6:
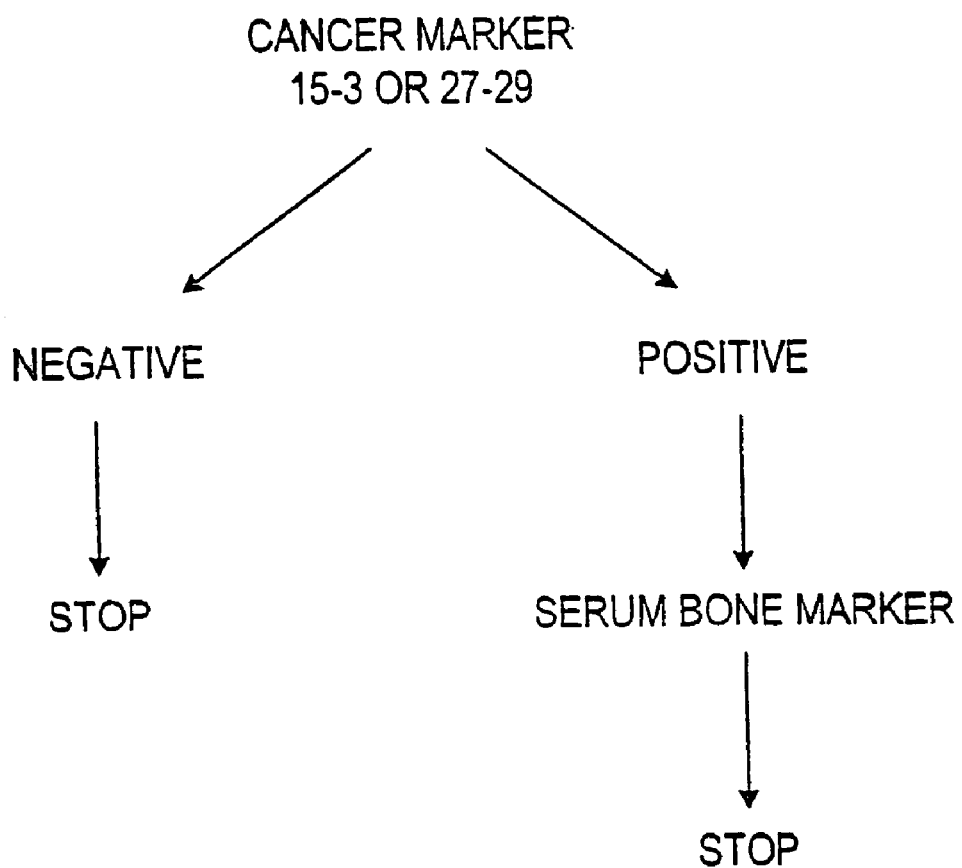
FIG. 6 is a diagram illustrating the breast cancer algorithm with the follow-up (n+1)st test dependent on the result of the nth assay; the algorithm measures cancer markers CA15.3 or 27.29 to denote normal or elevated levels; those samples having elevated levels are further analyzed for serum bone marker to provide a chemical staging of the malignant lesion.

FIG. 6 is a diagram illustrating the breast cancer algorithm with the follow-up (n+1)st test dependent on the result of the nth assay; the algorithm measures cancer markers CA15.3 or 27.29 to denote normal or elevated levels; those samples having elevated levels are further analyzed for serum bone marker to provide a chemical staging of the malignant lesion.

Breast cancer is the leading cancer of females (J. C. Bennet and F. Plum (eds), *Cecil Textbook of Medicine,* 20th edition (Philadelphia; W B Saunders), 1996.)

Breast carcinoma is monitored using a variety of markers e.g. carcinoembryonic antigen (CEA) and more recently the probably related tumor markers (CA-27.29 and CA 15.3). Many clinicians will use them in a quasi-diagnostic mode, obtaining the assay prior to the availability of definitive histopathologic data. Metastatic breast cancer is a bone seeking lesion. The algorithm exploits this connection to provide an early chemical diagnosis and staging of this lesion. The algorithm refers to CA15:3 as being either elevated or negative without denoting a specific number. This is because the manufacturer of the assay suggests that each laboratory define its own reference range depending on the composition of the population being served.

Although CA15.3 is issued as the starting assay in its breast cancer algorithm, the usefulness of this approach is not restricted by the choice of starting marker. Also, the principle of chemical staging of malignant lesions by algorithm can be applicable to other tumors as appropriate primary tumor markers and markers of metastases are identified. A significant benefit of this approach may be a decrease in the number of radiological studies looking for bone metastases in the staging of these lesions.

The chemical assays used in this algorithm are based on readily available immunoassay kits, the general principles of which are described. For example, tumor markers may be obtained from Abbott Diagnostic, Inc. and a bone marker from Ostex, Inc., although the utility of the algorithm is independent of the manufacturer assuming the latter has met the appropriate regulatory requirements.

CA 15-3: Cancer Antigen 15-3

The AxSYM CA 15-3 assay is a Microparticle Enzyme Immunoassay (MEIA) for the quantitative measurement of CA 15-3 assay values in human serum and plasma (EDTA) to aid in the management of Stage II and III breast cancer patients. Serial testing for patient CA 15-3 assay values should be used in conjunction with other clinical methods for monitoring breast cancer.

CA 15-3 assay values are defined by using the 115D98 and DF3 monoclonal antibodies. Monoclonal antibody 115D8, raised against human milk-fat globule membranes, and monoclonal antibody DF3, raised against a membrane enriched fraction of metastatic human breast carcinoma, react with epitopes expressed by a family of high molecular weight glycoproteins designated as polymorphic epithelial mucins (PEMs) in research studies have indicated that CA 15-3 assay values are frequently elevated in patients with breast cancer. These studies have suggested that the CA 15-3 assay may be of clinical value for monitoring the response of patients undergoing therapy because increasing and decreasing values correlated with disease progression and regression, respectively. Additional published studies have suggested that increasing CA 15-3 assay values in patients at risk for breast cancer recurrence after primary therapy may be indicative of recurrent disease before it can be detected clinically.

Elevations of CA-15-3 assay values have been reported in individuals with nonmalignant conditions such as cirrhosis, hepatitis, autoimmune disorders, and benign disease of the ovary and breast. Non-mammary malignancies in which elevated CA 15-3 assay values have been reported include lung, colon, pancreatic, primary liver, ovarian, cervical and endometrial. CA 15-3 assay values are not elevated in most normal individuals.

The CA 15-3 assay is not recommended as a screening procedure to detect cancer in the general population; however, use of the CA 15-3 assay as an aid in the management of breast cancer patients has been reported.

The AXSYM CA 15-3 assay is based on Microparticle Enzyme Immunoassay (MEIA) technology. MEIA technology uses a solution of suspended, submicron sized latex particles to measure analytes. The particles are coated with a capture molecule specific for the analyte being measured. The effective surface area of microparticles increases assay kinetics and decreases assay incubation time.

Reactants and sample for one assay are transferred to a reaction vessel (RV). In the RV, the reagents and sample are combined and then incubated to allow the reactants to come to reaction temperature. The reaction mixture is transferred to an inert glass fiber matrix, Irreversible binding of the microparticles causes the Immune complex to be retained by the glass fibers while the reaction mixture flows rapidly through the large pores in the matrix.

An Alkaline Phosphatase-labeled conjugate is added to the glass fiber matrix prior to the addition of 4-Methylumbelliferyl Phosphate (MUP). The conjugate catalyzes the hydrolysis of MUP to Methylumbelliferone (MU). Measurement of the fluorescent MU as it is generated on the matrix is proportional to the concentration of the analyte in the test sample.

This assay is unique in that the Calibrators are supplied prediluted: The AxSYM System dilutes all Controls and specimens by the same final dilution factor as the prediluted Calibrators during the course of the assay.

4.6. Prostate Cancer Algorithm

The NTx Test

Osteomark NTx Serum provides a quantitative measure of cross-linked N-telopeptides of type I collagen (NTx) in human serum as an indicator of bone resorption.

A Serum NTx level is used to aid in predicting skeletal response (bone mineral density) to antiresorptive therapy and in monitoring bone resorption changes following initiation of antiresorptive therapy. Prior to initiating antiresorptive therapy, a serum NTx level is used to determine the probability for a decrease in bone mineral density (BMD) after one year in postmenopausal women treated with hormonal antiresorptive therapy relative to those treated with calcium supplementation.

The measurement range of Osteomark NTx Serum is 3.2 to 40.0 nM Bone Collagen Equivalents (BCE).

Mammalian bone is continuously remodeled through a coupled process of osteoclast-mediate bone resorption, followed by osteoblast mediated bone formation. This process is necessary for normal development and maintenance of the skeleton. Abnormalities in this tightly coupled process often result in changes in skeletal mass and shape. The measurement of specific degradation products of bone matrix provide analytical data about the rate of bone metabolism. Approximately 90% of the organic matrix of bone tissue is type I collagen. Type I collagen, a helical protein that is cross-linked at the N-terminal and C-terminal ends of the molecule, forms the basic fabric and tensile strength of bone tissue.

The discover of cross-linked N-telopeptides of type I collagen (NTx) has provided a specific biochemical marker of human bone resorption which can be anlyzed by immunoassay. The NTx molecule is specific to bone due to the unique amino acid sequences and orientation of the cross-linked alpha-2(I) N-telopeptide. Generation of the NTxMolecule is mediated by osteoclasis on bone and found in urine and serum as a stable end-product of degradation.

Osteomark NTx Serum provides a quantitative measure of NTx in serum as an indicator of human bone resorption. Elevated levels of serum NTx indicate elevated bone resorption. Clinical research has demonstrated that elevated bone resorption is the primary cause of age-related bone loss and that low bone mass often results inosteopenia and is the major cause of osteoporosis. Osteoporotic fracture are reported to be the major source of increased morbidity and mortality in older women.

A randomized trial of postmenopausal women was conducted at eight clinical sites across the US. Subjects were randomized to either hormone replacement therapy (HRT) plus calcium supplements (500 mg daily) or calcium supplements alone. Serum samples collected during the study were tested using the Osteomark NTx Serum assay. Results of the testing support the use of Osteomark NTx Serum to monitor the antiresorptive effect of the therapy and to determine the probability for a decrease in BMD after one year if hormone therapy is not initiated.

A randomized, double-blind clinical study was conducted at a regional specialty hospital in postmenopausal women with low bone mass or diagnosed osteoporosis. Subjects were randomized to receive either placebo or 5–10 mg alendronate sodium. Serum samples collected during the study were tested using the Osteomark NTx Serum assay. Results obtained from this study support the utility of Osteomark NTx Serum to monitor the effect of antiresorptive therapy and to predict BMD response to therapy using early changes in the NTx serum value.

Osteomark NTx Serum is a competitive-inhibition enzyme-linked immunosorbent assay (ELISA/EIA) for quantitative determination of NTx in human serum.

NTX epitope is adsorbed onto a 96-well microplate. Diluted samples are added to the microplate wells, followed by a horseradish peroxidase labeled monoclonal antibody. NTx in the patient sample completes with the NTx epitope in the microplate well for antibody binding sites. Following a wash step, the amount labeled antibody bound is measured by colorimetric generation of a peroxide substrate. Absorbance is determined spectrophotometrically and NTx concentration calculated using a standard calibration curve. Assay values are reported in nanomoles Bone Collagen Equivalents per liter (nM BCE).

In the United States, prostate cancer is diagnosed in over 300,000 men each year and accounts for 24 percent of all newly diagnosed cases of cancer.

Prostate specific antigen (PSA) has been used in conjunction with digital rectal examination for early detection of prostatic cancer. Because of the elevation of serum PSA in benign prostate hyperplasia, PSA velocity and free PSA has been used to improve the detection of prostate cancer. PSA has mild protease activity and amino acid sequence homology with serine protease of the kallikrein family. It is expressed exclusively by normal, benign, hyperplastic and cancerous prostate glands but not by other tissues.

PSA exists in two major forms in blood circulation. The majority of PSA is complexed with protease inhibitor, $\alpha_1$-antichymotrypsin (ACT) (MW 100 000) or with $\alpha_2$-macroglobulin (A2M) and a minor component of free PSA (MW 28 430). Most immunoassays measure both free and ACT-complexed PSA but not A2M-PSA. In human seminal fluid, PSA could be fractionated into five ISO forms, PSA-A and PSA-B are active, intact enzymes capable of forming complexation with ACT. PSA-C, PSA-D, and PSA-E are nicked forms with disulfide bonds cleaved; they possess low or no enzymatic activities.

Figure 7:
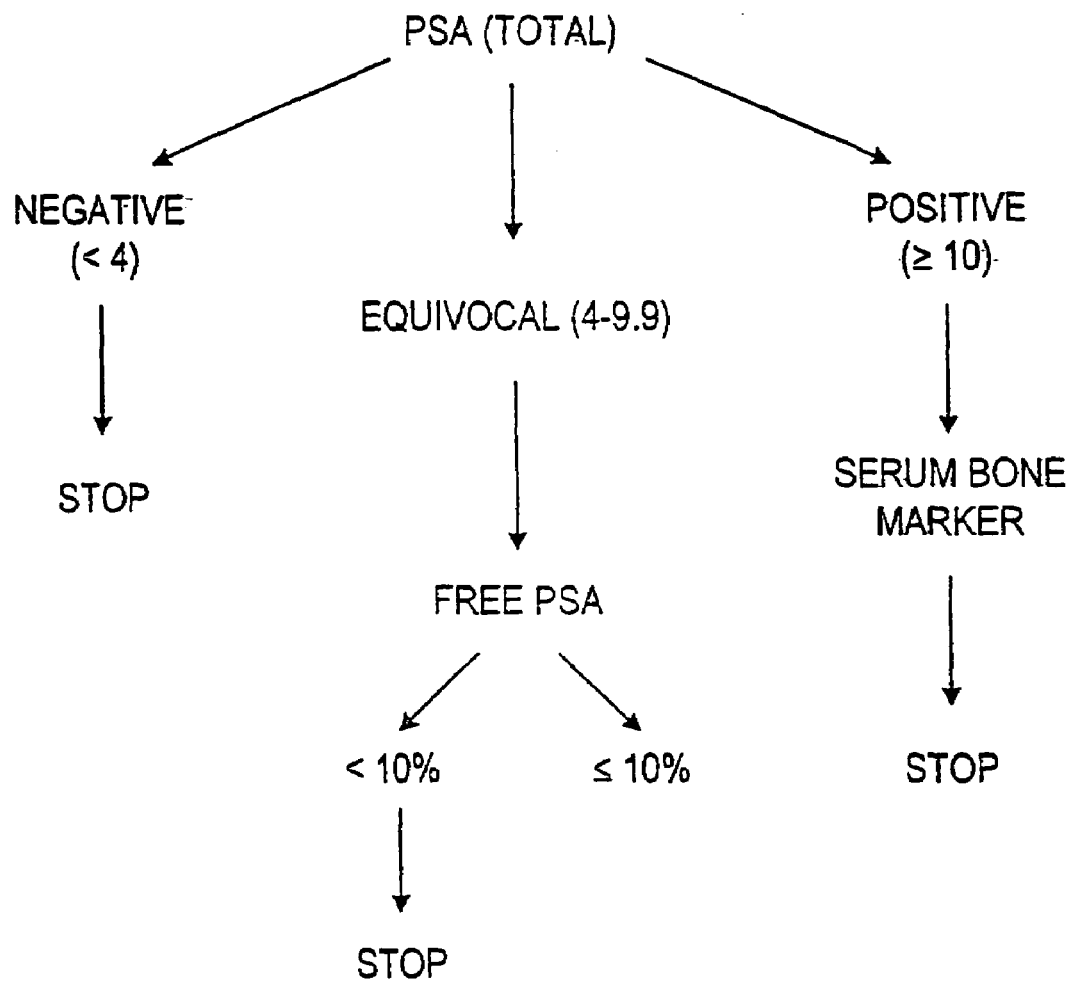
FIG. 7 is a diagram illustrating the prostate cancer algorithm with the follow-up (n+1)st test dependent on the result of the nth assay; the algorithm measures cancer marker PSA to differentiate samples having more or less than 10 mg/ml PSA. Samples having more than 10 mg/ml are further analyzed for the serum bone marker to provide a chemical staging of the malignant lesion. Samples having less than 5–10 mg/ml are measured for free PSA. If the result is more than 10% the test is terminated. If the result is less than 10%, the sample is further analyzed for the serum bone marker. If the total PSA measured at the start of the algorithm is <4 mg/ml the testing is stopped at this stage.

FIG. 7 is a diagram illustrating the prostate cancer algorithm with the follow-up (n+1)st test dependent on the result of the nth assay; the algorithm measures cancer marker PSA to differentiate samples having more or less than 10 mg/ml PSA. Samples having more than 10 mg/ml are further analyzed for the serum bone market to provide a chemical staging of the malignant lesion. Samples having less than 5–10 mg/ml are measured for free PSA. If the result is more than 10% the test is terminated. If the result is less than 10%, the sample is further analyzed for the serum bone marker. If the total PSA measured at the start of the algorithm is <4 mg/ml the testing is stopped at this stage.

Prostate Specific Antigen (PSA) is used as a screen and also for monitoring prostate carcinoma. Since enlargement of the prostate is common as men get older and some increase in serum PSA concentration occurs as a result, a method is needed to distinguish between benign and malignant prostate decease in instances with moderate elevation of PSA concentrations. This function is served by measurement of the proportion of PSA which is free as compared to protein bound. Metastatic prostate carcinoma if frequently "bone seeking" and such metastases will stimulate osteoclastic activity. Such activity can be monitored by a serum bone marker. Thus, the CLS algorithm will be efficient at the early detection of bone metastases as well as the distinction between benign and malignant prostate disease. Such information will have an effect on decisions regarding patient management.

The concentration of PSA in a given specimen, determined with assays from different manufacturers, can vary due to differences in assay methods and reagent specificity. The results reported by the laboratory to the physician must include the identity of the PSA assay used. Values obtained with different assay methods cannot be used inerchangeably. If, in the course of monitoring a patient, the assay method used for determining PSA levels serially is changed, additional sequential testing should be carried out. Prior to changing assays, the laboratory MUST confirm baseline values for patients being serially monitored.

PSA: Prostate Specific Antigen

The Abbott AxSYM PSA assay is a Microparticle Enzyme Immunoassay (MEIA) for the quantitative measurement of Prostate Specific Antigen (PSA) in human serum:

1. as an acid in the detection of prostate cancer when used in conjunction with digital rectal exam (DRE) in men aged 50 years or older. Prostatic biopsy is required for diagnosis of cancer.

2. as an adjunctive test used as an aid in the management of prostate cancer patients.

Prostate cancer is the most common type of of cancer found in men in the United States, with an incidence of approximately one case in every 10 men. Early diagnosis of carcinoma of the prostate is hindered by the lack of symptoms in men with localized tumors. Therefore, early detection requires a simple, safe, and inexpensive test for the disease in asymptomatic men. The traditional method for detection of prostate cancer is the digital rectal examination (DRE). However, only 30% to 40% of cancers detected by DRE screening are expected to be confined to the prostate. In January, 1992, the American Urological Association (AUA) endorsed annual examination for early detection of prostate cancer with DRE and PSA beginning at age 50. This was reaffirmed by the American Cancer Society (ACS) in November 1992.

The frequent finding of locally advanced prostate cancer in screened patients may be due to the inability of DRE to detect tumors of small volume that are most likely to be confined to the prostate. Since patients with small size tumors are believed to have the best prognosis, it can be concluded that DRE has limited sensitivity in detecting those tumors with the greatest potential for cure. In a 1990 publication by Cooner, et al., data was presented regarding the clinical use of other diagnostic modalities such as prostate ultrasonography and serum prostate specific antigen (PSA) for early detection of prostate cancer. This study found that there was a significant increase in predictability for cancer when the DRE and PSA tests were abnormal.

Several other studies have shown that the measurement of serum PSA concentrations offer several advantages in the early detection of prostate cancer. The procedure is more acceptable to patients, the result is objective and quantitative and is independent of the examiner's skill. In several recent studies of healthy men 50 or more years old, serum PSA levels had the greatest ability to predict prostate cancer. These studies concluded that not only is serum PSA measurement a useful addition to rectal examination and ultrasonography in the detection of prostate cancer but that it is also the most accurate of the three tests for this purpose.

PSA testing can have significant value in detecting metastatic or persistent disease in patients following surgical or medical treatment of prostate cancer. Persistent elevation of PSA following treatment or increase in a post-treatment PSA level is indicated of recurrent or residual disease. PSA testing is widely accepted as an adjunctive test in the management of prostate cancer patients.

AxSYM PSA is based on the Microparticle Enzyme Immunoassay (MEIA) technology.

The AxSYM PSA Reagents and sample are pipetted in the following sequence:

Sample and all AxSYM PSA reagents required for one test are pipetted by the Sampling Probe into various wells of a reaction vessel (RV). The RV is immediately transferred into the Processing Center. Further pipetting is done in the Processing Center by the Processing Probe.

The reactions occur in the following sequence:

Sample, Anti-PSA Coated Microparticles and Assay Diluent are pipetted to one well of the reaction vessel. During the incubation of this reaction mixture the PSA in the specimen binds to the Anti-PSA Coated Microparticles forming an antibody-antigen complex.

An aliquot of the reaction mixture is transferred to the matrix cell. The microparticles bind irreversibly to the glass fiber matrix.

The matrix cell is washed to remove unbound materials.

The Anti-PSA: Alkaline Phosphatase Conjugate is dispensed onto the matrix cell and binds to the antibody-antigen complex.

The matrix cell is washed to remove unbound materials.

The substrate, 4 Methylumbelliferyl Phosphate, is added to the matrix cell and the fluorescent product is measured by the MEIA optical assembly.

Free PSA (Prostate Specific Antigen)

The AxSYM Free PSA assay is a Microparticle Enzyme Immunoassay (MEIA) for the quantitative measurement of free prostate specific antigen (PA) in human serum. The AxSYM Free PSA assay is intended to be used in conjunction with the AxSYM PSA assay to determine the ratio of free PSA to total PSA.

Prostate specific antigen (PSA), a member of the human Kalilikrein gene family, is a serine protease with chymotrypsin-like activity. The mature form of PSA is a single chain glycoprotein of 237 amino acids containing 7–8% carbohydrate as a single N-linked oligosaccharide side chain. PSA has a molecular weight of approximately 30,000 daltons. The major site of PSA production is the glandular epithelium of the prostate. PSA produced by the prostate is secreted into the seminal fluid in high concentrations. PSA is also present in urine and serum. The function of PSA is the proteolytic cleavage of gel forming proteins in the seminal fluid resulting in liquification of the seminal gel and increased sperm motility. Low levels of PSA are found in the blood as a result of leakage of PSA from the prostate gland. Increasing levels of PSA are associated with prostatic pathology; including prostatitis, benign prostatic hyperplasia (BPH), and cancer of the prostate.

PSA occurs in three major forms in the blood. The major immunodetectable form is PSA complexed with the serine protease inhibitor, alpha-1-antichymotrypsin (PSA-ACT). Uncomplexed, or free PSA, is the other immunodetectable form of PSA in serum. The majority of free PSA in serum appears to be an inactive from that cannot complex with protease inhibitors and may be either a PSA zymogen or an enzymatically-inactive, cleaved form of PSA. A third form of PSA, a complex with alpha-2-macroglobulin (AMG), is not detectable with current immunoassays for PSA due to the engulfment and subsequent masking of PSA epitopes by the alpha-2-macroglobulin molecule.

Immunoassays have been designed to detect free PSA, PSA-ACT complex, and total PSA (immunodetectable forms: e.g. free PSA and PSA-ACT). Using these types of assays, the proportion of free PSA in the serum was found to be significantly higher in patients with BPH than in patients with prostate cancer ($p<0.0001$). The proportion, or percent, of free PSA determined by comparing the concentration of free PSA to the concentration of total PSA has been proposed as a way to improve the discrimination between BPH and prostate cancer especially in those men with intermediate levels of total serum PSA.

4.7. Epstein-Barr Virus Algorithm

Epstein-Barr virus (EBV), the etiologic agent of infectious mononucleosis (IM), has a worldwide distribution, with 80 to 90% of all adults having been infected. In most cases of IM, clinical diagnosis can be made from symptoms of fever, pharyngitis and cervical lymphadenopathy lasting 1 to 4 weeks. Normally a self-limiting illness, IM may be complicated by splenomegaly, hepatitis, pericarditis, or central nervous system involvement. Hematologic features of IM include lymphocytosis with prominent atypical lymphocytes. In 85 to 90% of IM patients, Paul Bunnell heterophile tests are positive. False positives may occur in 2 to 3% of patients and can be excluded only by EBV-specific serology. Specific laboratory diagnosis is needed to differentiate the 10 to 15% of heterophile—negative EBV infections from mononucleoses induced by other agents such as cytomegalovirus, adenovirus and *Toxoplasma gondii*. Owing to the ubiquity of EBV in sero positive individual, it has been difficult to ascertain the degree of morbidity attributable to EBV reactions. EBV is unique among the herpes viruses in its ability to transform and immortalize human B lymphocytes. In vitro, EBV—infected lymphoid cells are associated with several lymphoproliferative conditions varying from hyperplasia to cancer. EBV has been implicated in the etiology of Burkitt's lymphoma and nasopharyngeal carcinoma.

On the molecular level, EBV strains may be classified into types A and B on the basis of organization of their EBNA genes. Generally, only a single acute phase serum sample of 1 to 5 ml, is needed for the diagnosis by serologic testing. Convalescent phase serum collected 1 to 2 months after onset is occasionally needed. Samples can be stored at 5° C. for several months and for longer storage, frozen at −20° C.

FIG. 8 is a diagram illustrating the Epstein-Barr Virus Algorithm with the follow-up (n+1)st test dependent on the result of the nth assay; the algorithm yields results in cases which are heterophile antibody negative (10–20%) as well as covering those cases which would be heterophile antibody positive; the result obtained with antibody to EBV early antigen D may be negative to indicate that the next step should be the test with antibody to viral capsid antigen. The result may be positive to indicate that the next step should be to test with antibody to E-B nuclear antigen IgG.

Epstein-Barr Virus infection is the etiologic agent of infectious mononucleosis, (IM) and is also associated with nasopharyngeal carcinoma and lymphoproliferative disorders. Details may be found in any standard textbook of Medicine (J. C. Bennett and F. Plum (eds), *Cecil Textbook of Medicine*, 20th edition (Philadelphia; W B Saunders), 1996.)

Historically, diagnosis of acute IM was done using tests to detect heterophile antibody. Such tests perform relatively satisfactory in adolescents and young adults but have reduced sensitivity outside this age group. Also titers of antibodies to various EBV antigens especially early antigen are useful in monitoring therapy for nasopharyngeal carcinoma.

The algorithm is useful in the diagnosis of infectious mononucleosis especially because it yields diagnostically useful results in cases which are heterophile antibody positive. The algorithm requires the minimum number of steps with the resulting pattern of test outcomes conveying immediately relevant information to the clinician.

General principles of the assays utilized are described. These tests are immunoassays which detect the relevant antibodies in patient samples through reaction with antigen molecules adherent to a solid surface. Although kits are obtained from Diasorin, Inc., the utility of the algorithm is independent of the kit manufacturer as long as the latter is approved by the appropriate regulatory bodies.

The Clin-ELISA™ EBV Early Antigen (D) IgG test Kit utilizes the enzyme-linked immunosorbent assay (ELISA) technique for the detection of Epstein-Barr Early Antigen (Diffuse) IgG antibodies. Diluted patient serum is incubated with recombinant EA bound to the solid surface of a microtitration well. If specific antibodies are present in the patient's serum, antigen antibody complexes are formed. The complexes bind with alkaline phosphatase labeled antihuman IgG which react with the addition of para-Nitrophenyphosphate (p-NPP) substrate, resulting in color development. The absorbance of the solution, measured at 405 nm, is directly related to the concentration of IgG to EA (D).

The DiaSorin Epstein-Barr Viral Capsid Antigen test kit utilizes the enzyme-linked immunosorbent assay (ELISA) based on the antibody capture technique. Diluted patient serum is incubated with mouse monoclonal antibody against human IgM (μchain specific) bound to the solid surface of the microtiter well. Patient IgM is "captured" by the surface bound antibody. The presence of patient anti-VCA IgM antibodies are then "detected" and bound by VCA p18 peptide antigen which is linked to an anti-p18 monoclonal antibody conjugated to horseradish peroxidase. Bound horseradish peroxidase is reacted with chromogen/substrate solution resulting in color development. The absorbance of the solution, measured at 450 nm, is related to the concentration of IgM to Epstein-Barr Viral Capsid Antigen present in the reaction solution.

The DiaSorin Epstein Barr Nuclear Antigen IgG test kit utilizes the enzyme-linked immunosorbent assay (ELISA) technique for the detection of Epstein-Barr Nuclear Antigen (EBNA) IgG antibodies. Diluted patient serum is incubated with EBNA-1 peptide bound to the solid surface of a microtiter well. If EBNA-1 antibodies are present in the patient's serum, antigen-antibody complexes are formed. These complexes bind with horseradish perioxidase-labeled antihuman IgG which react with the addition of chromogen/ substrate, resulting in color development. The absorbance of the solution, measured at 450 nm, is related to the concentration of IgG to Epstein-Barr Nuclear Antigen.

4.8. Thyroid Function Algorithm

The two major goals of thyroid function tests are to assess the amount of circulating thyroid hormone and to explain the findings obtained by physical examination of the gland. The active circulating thyroid hormones are tetra iodothyronine ($T_4$) and tri iodothyronine ($T_3$).

The measurement of serum thyroid stimulating hormone (TSH) level is the preferred approach to assessing the functional state of the thyroid gland because: i) TSH is central to the negative feedback system; ii) TSH responds logarithmically to arithmetic changes in serum thyroid hormone level; and iii) TSH assays can now detect both elevation of TSH levels and pathophysiologically significant lowering of TSH levels.

The total serum $T_4$ level, which is measured by competitive protein binding or radioimmuno assay, comes closest to reflecting the functional state of the thyroid gland in most patients. The $T_4$ level is high in approximately 90 percent of hyperthyroid patients and low in approximately 85 percent of hyperthyroid patients. This sensitivity should make the measurement of the $T_n$ level an excellent test for hyperthyroidism. However, the specificity of the total serum $T_4$ level for hyperthyroidism is much lower because many factors elevate the level of thyroxine-binding proteins and therefore raise the serum $T_4$. These factors include pregnancy, oral contraceptives, estrogens, acute infections hepatitis and genetic alteration. In addition, many circumstances other than hyperthyroidism raise the serum $T_4$ level without altering the level of thyroxine-binding globulin, e.g. increased biding of $T_4$ to serum albumin acute nonthyroid illness and some drug effects. Additional function tests may be required to clarify resultant changes in the serum $T_4$ level. Because most of the alterations of total $T_4$ do not affect the level of free, or unbound $T_4$ ($FT_4$), it is often useful to measure this value. There are two approaches to measuring $FT_4$: resin $T_3$ uptake ($RT_3U$) and direct measurement.

Figure 10:
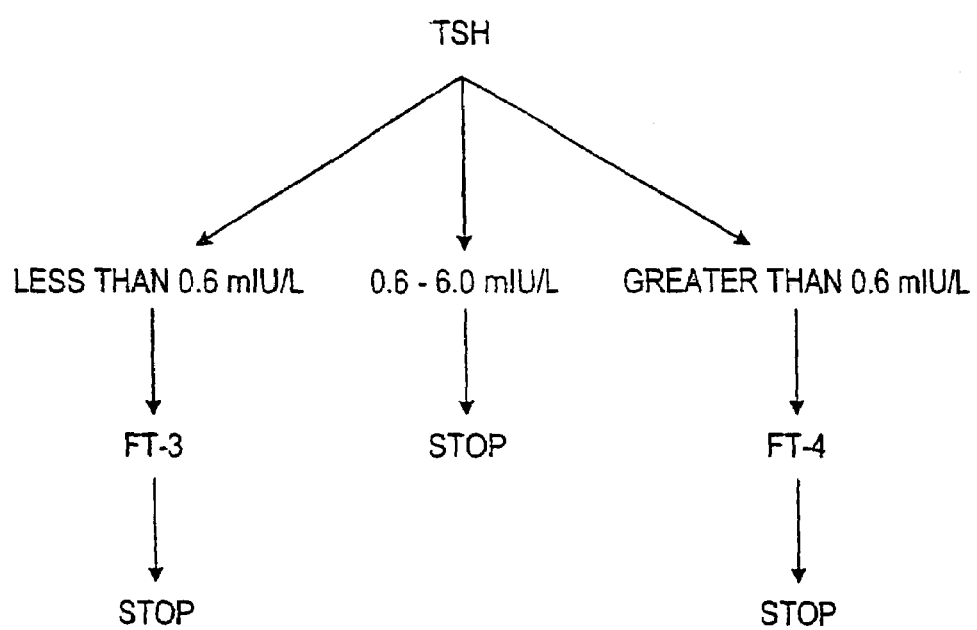
FIG. 10 is a diagram illustrating the thyroid function algorithm with the follow-up (n+1)st test dependent on the result of the nth assay; the algorithm measures total TSH, $FT_3$ and $FT_4$.

FIG. 10 of the present invention describes thyroid function algorithm.

The diagnosis of thyroid disease has historically involved the use of thyroxine (T-4) and a tri-iodothyronine (T-3) or T-4 resin uptake test to "correct" for protein binding effect. Problems with false positive and false negative test results and the development of high sensitivity thyroid stimulating hormone (TSH) and free hormone assays (FT-4 and FT-3) have permitted the development of an algorithm which allows for accurate diagnosis while rapidly turning around negative results for which no further thyroid testing would be required. The basic physiology of thyroid function means that a decrease in the primary thyroid hormones (T-3/T-4) will through a negative feedback loop cause an increase in the TSH concentration and vice versa. TSH values are therefore the most sensitive index of thyroid status.

In affluent countries where iodine deficiency is no longer a consideration, Hashimoto's thyroiditis is probably the leading cause of hypothyroidism. Grave's Disease is the leading cause of hyperthyroidism. These are autoimmune diseases and because there is some evidence of a genetic contribution, these diagnosis may be important for purposes of screening family members. Antibodies to thyroid peroxidase (otherwise known as anti-microsomal antibodies), interestingly are common to both Grave's Disease and Hashimoto's thyroiditis and may be used to help define the etiology of the thyroid dysfunction.

The Chiron Diagnostics ACS:180 TSH assay is a two-site sandwich immunoassay using direct, chemiluminometric technology, which uses constant amounts of two antibodies. The first antibody, in the Lite Reagent, is a monoclonat mouse anti-TSH antibody labeled with acridinium ester. The second antibody, in the Solid Phase, is a polyclonal sheep anti-TSH antibody which is covalently coupled to paramagnetic particles.

The Chiron Diagnostics ACS:180 FrT4 assay is a competitive immunoassay using direct, chemiluminometric technology. $FT_4$ in the patient sample competes with acridinium ester-labeled $T_4$ in the Lite Reagent for a limited amount of polyclonal rabbit anti-$T_4$ antibody, which is covalently coupled to paramagnetic particles in the Solid Phase.

The Chiron Diagnostics ACS:180 FT3 assay is a competitive immunoassay using direct, chemiluminometric technology. $FT_3$ in the sample with a $T_3$ analog, which is covalently coupled to paramagnetic particles in the Solid Phase for a limited amount of acridinium ester-labeled monoclonal mouse anti-$T_3$ antibody in the Lite Reagent.

Autoimmune thyroid disease is characterized by the presence of circulating autoantibodies directed to thyroid antigens. Hasimoto and Graves diseases are the best known of these diseases. The majority can be diagnosed by clinical presentation and their antibody profiles to thyroglobulin and thyroid microsomes. Therefore, immunoassays for thyroid antibodies are useful for diagnostic evaluations of thyroid autoimmune disease.

Classically, autoantibodies to thyroid antigens are detected by precipitation reactions, hemagglutination and by immonufluorescence. However, the tests are subjective and lack high sensitivity. Enzyme-Linked Immunosorbent Assays (ELISAs) combine greater sensitivity, objective reading and ease of use. ELISAs have been developed and validated for detecting autoantibodies to thyroid antigens.

The Wampole Microsomal test is an Enzyme-Linked Immunosorbent Assay to detect IgG, IgM, and IgA antibodies to microsomal antigens. Purified microsomal antigens are attached to a solid phase microassay well. Diluted test sera are added to each well. If the antibodies are present that recognize the antigen, antigen-antibody complexes are formed.

4.9. Autoimmune Algorithm

The detection of circulating antibodies to nuclear antigens is an important tool in the diagnosis of systemic rheumatic and other autoimmune diseases. The most widely used technique for detecting antinuclear antibodies (ANA) is the fluorescent—ANA test. It is used to screen sera before other techniques such as immunodiffusion, counter immuno electrophoresis, radioimmuno assay, enzyme immuno assay (EIA), immuno precipitation and immunoblotting are used to define antibody specificity. The FANA test has the advantages of economy, sensitivity, reproducibility and relative ease of performance. The ANA of patients with systemic rheumatic diseases binds to nuclear components from various species. The FANA test confirms the clinical diagnosis of diseases such as systemic lupus erythematosus (SLE), systemic Sclerosis or Sjojren's syndrome. Since 2 to 5% of untreated SLE patients and 10 to 15% of Systemic Sclerosis patients can have a negative FANA test result, this test does not rule out the diagnosis of these diseases. In addition, patients receiving a drug such as procainamide, hydralazine or any of a growing list of other drugs are tested if they are presented with symptoms suggesting a diagnosis of drug-induced lupus.

If the FANA test is positive at screening dilutions of 1:4 and 1:16, further dilutions of 1:64 and 1:256 are prepared and the test is repeated. This is important so as to determine the titer of antibodies present and because the pattern or intensity of nuclear fluorescence changes upon dilution of the serum. The immunofluorescence pattern of staining provides clues to the category of nuclear antigens involved and is divided into 5 categories: homogeneous, sparkled, nucleolar, other nuclear and cytoplasmic. For example, antibodies to DNA and histone give a homogenous or rim pattern.

Native DNA (NDNA) antibodies (anti-nDNA) re important in the diagnosis and management of patients with SLE. These auto-antibodies are rarely found in patients with other rheumatic diseases.

Systemic lupus erythematosus (SLE) is the paradigm of autoimmune disease. The course of this chronic multisystemic inflammatory disease may range from benign to fatal with annual incidence of about seven cases per 100,000, 90% SLE occurs in women and the first symptoms usually appear between 15 and 25 years of age. SLE produces lesions in the kidneys, blood vessels, pleura, central nervous system and skin.

Some of the most characteristic of the numerous auto antibodies formed in SLE are the antinuclear antibodies (ANA). More than 90% of patients with SLE have positive antinuclear antibody tests. However, the test is positive in several other conditions and in some elderly patients who are without apparent disease. Although a repeatedly negative test makes the SLE diagnosis unlikely 5 to 10 percent of patients in whom the diagnosis is well established will test negatively. Most ANA—negative patients have circulating antibodies to the cytoplasmic antigens Ro and La and to single-stranded DNA. Such patients usually have photosensitive dermatitis, a low incidence of renal and central nervous system involvement, and a good prognosis.

Figure 11:
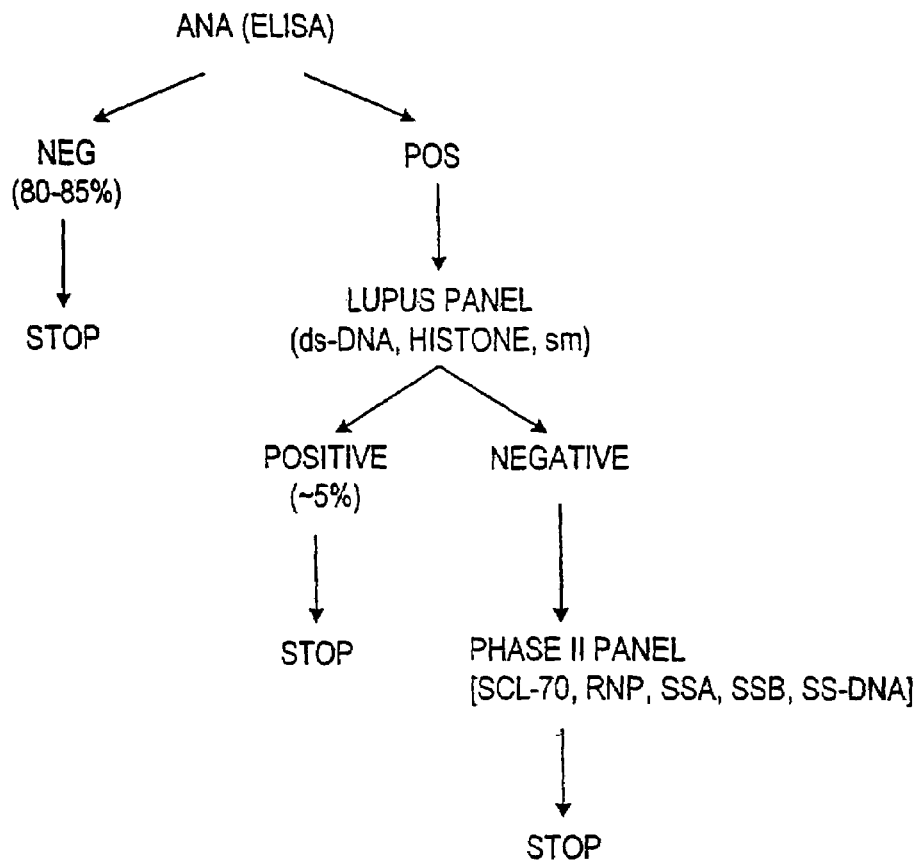
FIG. 11 is a diagram illustrating the autoimmune algorithm with the follow-up (n+1)st test dependent on the result of the nth assay; the algorithm comprises a test for ANA, which if positive is continued to test for diagnosis of lupus using Ds-DNA, histone and Sm; if the test results are negative, then analysis is continued using the next panel of tests including SCL-70, RNP, SSA, SSB, SS-DNA.

FIG. 11 is a diagram illustrating the autoimmune algorithm with the follow-up (n+1)st test dependent on the result of the nth assay; the algorithm comprises a test for ANA, which if positive is continued to test for diagnosis of lupus using Ds-DNA, histone and Sm; if the test results are negative, then analysis will be continued using the next panel of tests including SCL-70, RNP, SSA, SSB, SS-DNA.

A collection of diseases known as collagen vascular diseases which include Systemic Lupus Erythematosis (SLE), Scleroderma, Sjogren's Syndrome and Mixed Connective Disease (MCTD) are characterized, from the laboratory perspective, by the appearance of antibodies against self-antigens. Details can be found in any standard textbook of Medicine (J. C. Bennett and F. Plum (eds), *Cecil. Textbook of Medicine,* 20th edition (Philadelphia; W B Saunders), 1996.). The most frequent of these is anti-nuclear antibody (ANA). This test is highly sensitive (a negative result essentially rules out one of these diseases) although it is not completely specific since a positive result can occur in the elderly without evidence of concurrent collagen vascular disease.

Usually the tests in the algorithm are offered as part of a collagen vascular disease profile or panel. Thus, all tests are done even if the ANA is negative. It is found that 80–85 percent of assays submitted for ANA testing are in fact negative. By making the execution of the subsequent assays dependent on the results of the preceding test(s) the current algorithm saves un-necessary testing. This is a general feature of an algorithmic approach to laboratory testing.

The general principles of the assays used in this algorithm are described. They are standard immunoassays manufactured by several companies and ready available to the typical clinical laboratory. The assays are run on a highly automated immunoassay plate processor connected to the laboratory computer.

The TheraTest EL-ANA screen is an enzyme immunoassay which screens human serum for the presence of anti-nuclear antibodies (ANAs). The test detects multiple ANAs including anti-double-stranded DNA (dsDNA), anti-single stranded DNA (ssDNA), antiSm, anti-RNP, anti-SSA(Ro), anti-SSB, anti-Scl-70, antihistone and anti-Jo-1. It also detects antibodies in sera that produce different immunofluorescent (IFA) patterns: speckled, nucleolar, homogenous, preripheral and centromere.

The TheraTest EL-ANA screen is a solid phase enzyme immunoassay test. The microwells of a polystyrene plate have been coated with the antigens. Two different microwells, A and B (these are NOT duplicates) are incubated with Patient Specimens, Controls and Calibrators. During the incubation, the antibody present in the test sample binds to the solid phase. The microwells are washed and horseradish peroxidase labeled goat anti-human IgG (Fc γ specific) is incubated in the wells. After another wash, a specific substrate is added and autoantibody binding is detected by a color change which is analyzed using a spectro-photometric enzyme immunoassay reader. All specimens that yield absorbance values higher than the cut-off calibrator for A and/or b well are considered positive. They may be tested further by IFA it pattern identification is desired or by specific antinuclear antibody panels of tests. Specimens with values lower than the cut-off calibrator do riot required additional testing.

Figure 12:
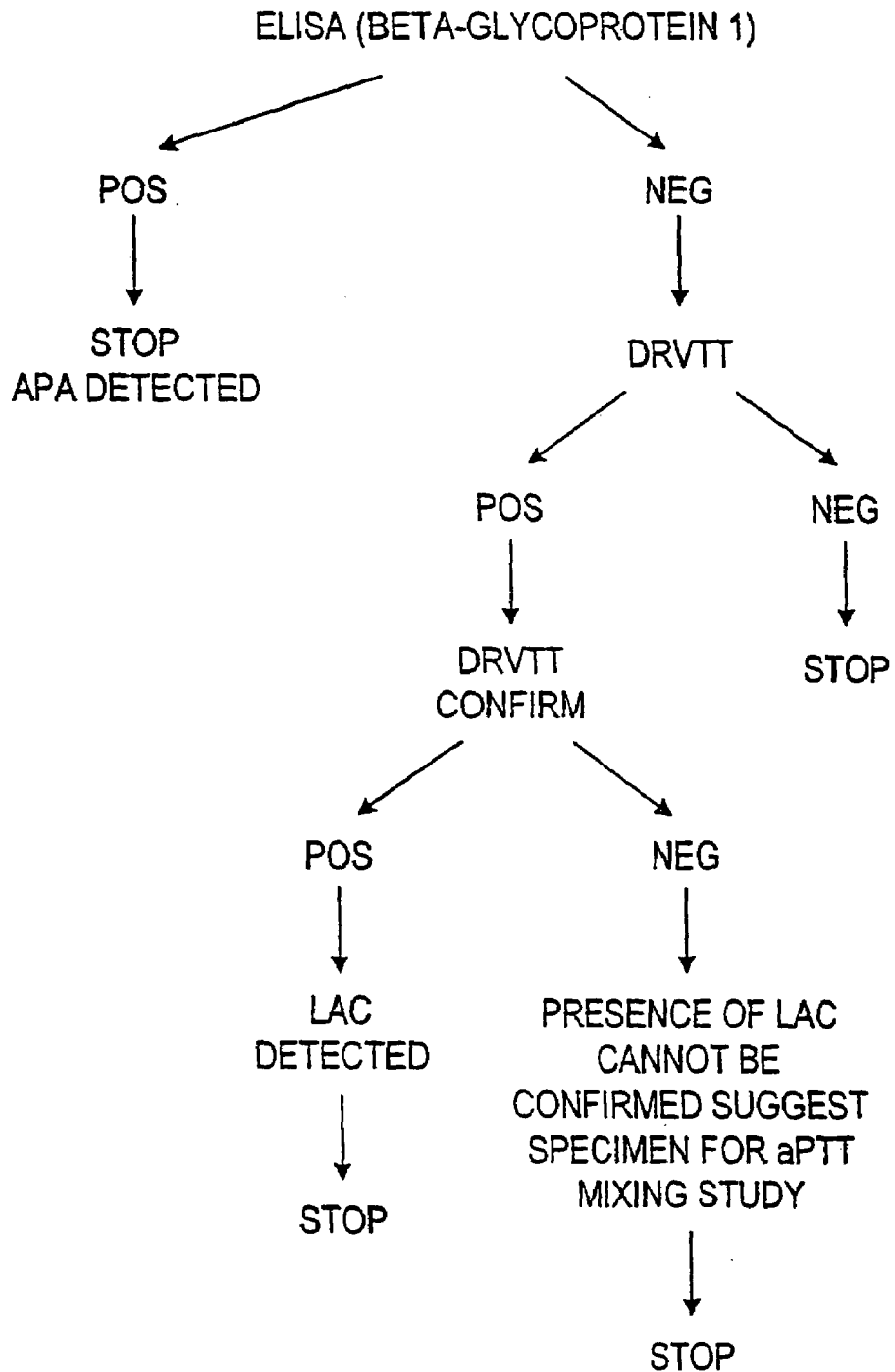
FIG. 12 is a diagram illustrating the serum protein algorithm with the follow-up (n+1)st test dependent on the result of the nth assay; the algorithm comprises identification of an abnormal immunoglobulin using serum protein electrophoresis and if the result is positive, the class of immunoglobulin is identified and quantitated by immunofixation electrophoresis.

FIG. 12 describes the lupus anticoagulant/APA algorithm

Lupus anticoagulants/anti-phospholipid antibodies (LAC/APA) are associated with arterial and venous thrombosis (K. S. Ginsberg et al, *Ann. Int. Med.* 117:997 (1992) and (Finazzi et al, *Am. J. Med.* 100:530 (1996)).

Assays for lupus anticoagulants (LAC) and anti-phospholipid antibodies (APAs) can be performed using the activated partial thromboplatin time (aPTT) and/or dilute Russell viper venom time (DRVTT) [coagulation testing], or by testing for APA's using an immunoassay (ELISA) methodology. Other coagulation test that have been suggested for the detection of Lupus Anticoagulants include the Kaolin clotting time (KCT) and the dilute prothrombin time (dPT). It has been suggested that more than one coagulation test be used for assessing the presence of LAC. There is, however, scant material in the medical literature with respect to the cost and benefit of such an approach. Should multiple coagulation tests become generally accepted laboratory practice, the structure of the algorithm would still not be affected. Current research suggests that an immunoassay which detects antibodies to Beta-Glycoprotein 1 should be used. The latter are more likely to be of autoimmune as opposed to infectious etiology and these are the antibodies which appear to be associated with thrombosis. The CLS protocol assays for antibodies to Beta-Glycoprotein 1 of all classes i.e. IgG, IgM and IgA. APA are recognized as being heterogeneous in their target antigens. As reagents that allow detection of APA directed against proteins such as prothrombin and annexin V become available, the algorithm might be improved by their inclusion in the screening step. Although the coagulation based and immunoassay methods are frequently concordant, there are occasions when the two methods give discrepant results.

The CLS algorithm combines immunologic and functional assays so as to maximize detection in the minimum number of steps. It differs from conventional approaches which do not combine both aspects of the test procedure algorithmically.

The general principles upon which the CLS approach is based are appended. the methodologies employed are readily available to the clinical laboratory. Although CLS uses the DRVTT as its coagulation assay the same algorithmic structure would be applicable whichever coagulation assay or assays were employed.

Lupus anticoagulants (LA) belong to the group of antiphospholipid antibodies which are directed against negatively charged phospholipids or complexes between phospholipids and proteins. When determined by their ability to prolong phospholipid-dependent tests (APTT, KCT, DRVTT) these antibodies are referred to as LA.

A semiquantitative enzyme linked immunoassay for detecting IgG class autoantibody to Beta2 glycoprotein I (Beta2 GPI) for use as an aid in the diagnosis of certain autoimmune disease thrombotic disorders, such as those secondary to SLE or other lupus like thrombotic diseases.

QUANTA Lite™ Beta2 GPI IgG is an enzyme linked immunoassay (ELISA) for the detection of antibodies in human serum to Beta2 GPI employing the sandwich ELISA technique.

A semiquantitative enzyme linked immunoassay for detecting IgA class autoantibody to Beta2 glycoprotein I (Beta2 GPI) for use as an aid in the diagnosis of certain autoimmune disease thrombotic disorders, such as those secondary to SLE or other lupus like disorders.

QUANTA Lite™ Beta2 GPI IgA is an enzyme linked immunoassay (ELISA) for the detection of antibodies in human serum to Beta2 GPI employing the sandwich ELISA technique.

4.10. Serum Protein Algorithm

Methods for the analysis of proteins in body fluids include: 1) specific quantitative assays of particular proteins by immunochemical methods using specific antisera and measurement of the antigen-antibody complexes by nephelometry, turbidimetry, or electroimmuno assay; or if present in very low concentrations, by R+A or enzyme immunoassay; 2) detection and identification of proteins by electrophoresis; 3) quantitative measurements of total protein in serum, urine and CSF; and 4) analysis by mass spectrometry which provides structural and quantitative information.

Electrophoresis is widely used in clinical laboratories to study and measure the protein content of biological fluids. If a single clone of plasma cells produces immunoglobulin molecules, the concentration of its particular protein in the patient's serum becomes so great that it can be measured by electrophoresis. The monoclonal immunoglobulins, which are also called paraproteins, may be polymers, monomers, or fragments of immunoglobulin molecules. About 60% of paraproteins are due to multiple myeloma or to a solitary plasmacytoma; about 15% are due to overproduction of B lymphocytes, mainly in lymph nodes, lymphomas or chronic lymphocytic leukemia; up to 25% of paraproteins are benign and many are never discovered.

Figure 13:
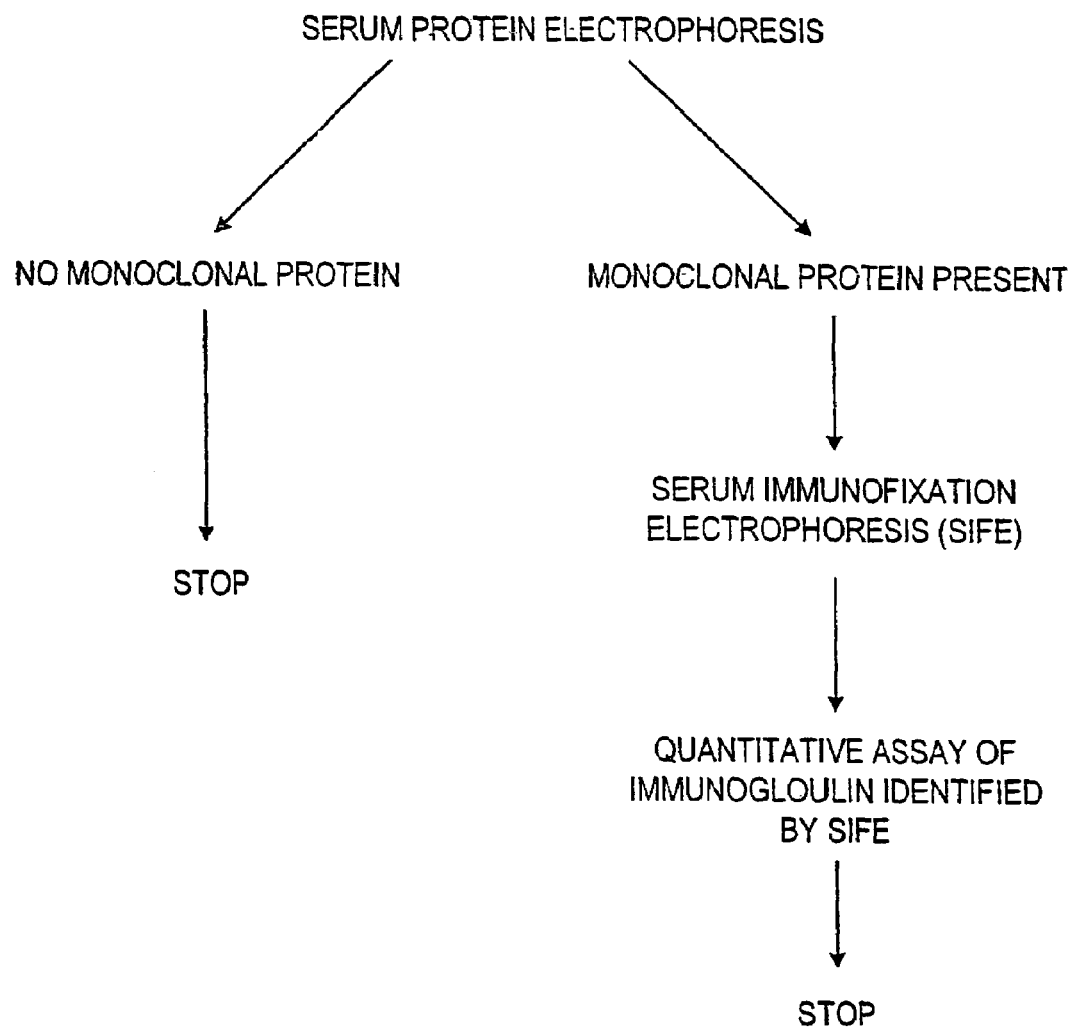
FIG. 13 is a diagram illustrating the lupus anticoagulant/APA algorithm comprising measurement of beta-glycoprotein 1, DRVTT, and LAC.

FIG. 13 is a diagram illustrating the serum protein algorithm with the follow-up (n+1)st test dependent on the result of the nth assay; the algorithm comprises identification of an abnormal immunoglobulin using serum protein electrophoresis and if the result is positive, the class of immunoglobulin is identified and quantitated by immunofixation electrophoresis.

The diagnosis of monoclonal gammopathies (Multiple Myeloma, Waldenstrom's Macroglobulinemia) and monitoring of therapy involves detection, identification and quantification of the abnormal proteins. Descriptions of the clinical aspects of these disease entities maybe found in any standard textbook of Medicine or Hematology (G. R. Lee et al, (eds) *Wintrobe's Clinical Hematology*, 9th edition: (Philadelphia: Lea & Febiger), 1993.

Initial identification of an abnormal immunoglobulin in performed using serum protein electrophoresis (SPEP) while identification of the immunoglobulin class involves serum immunofixation electrophoresis (SIFE). Quantification of the protein is best done using an immunoturbidimetric or immunonephelometric assay, although a less precise quantification can be accomplished using SPEP. These techniques are applicable to urine and cerebrospinal fluid, as well as serum.

Historically these tests were either ordered as a panel so all tests were performed regardless of whether an abnormal protein was present or not. The algorithmic approach accesses second and third level tests only if an abnormal protein is identified on the first test. Quantification of the abnormal protein by immunoturbidimetric/nephelometric techniques is performed to provide a baseline against which the clinical can monitor the effect of therapy.

The principal use of protein electrophoresis is in the detection of monoclonal gammopathies. These are usually found in association with hematopoietic neoplasms, esp. Multiple myeloma and macroglobulinemia of waldenstrom. Other applications of SPE include nutritional status, workup for liver disease, analbuminemia and bisalbuminemia. Decreased Total Protein with essentially normal pattern might indicate dietary deficiency or hemodilution. Significantly elevated T. Protein with essentially normal pattern is likely to be secondary to dehydration. Significantly low T. Protein and Albumin, increased Alpha2 and low gamma is prototypical of Nephrotic syndrome.

The sample, containing IgM, is mixed with a solution containing a high concentration of antibody, goat anti-IgM. The antigen—antibody complexes formed precipitate out of solution causing turbidity which is proportional to the immunoglobulin concentration. Absorbance of this solution is read at 340 nm. Polymer enhancement by polyethylene glycol (PEG) allows the reaction to reach endpoint rapidly, increases sensitivity, and minimizes the risks of obtaining falsely low results in samples with antigen excess.

The sample, containing IgA, is mixed with a solution containing a high concentration of antibody, goat anti-IgA. The antigen-antibody complexes formed precipitate out of solution causing turbdity which is proportional to the immunglobulin concentration. Absorbance of this solution is read spectrophotometrically. Polymer enhancement by polyethylene glycol(PEG) allows the reaction to reach endpoint rapidly, increases sensitivity, and minimizes the risk of obtaining falsely low results in sample with antigen excess.

Polyclonal IgG increases may be present in systemic lupus erythematosis, chronic liver diseases, and cystic fibrosis. Decreased synthesis of IgG is found in congenital and acquired immunodeficiency diseases and selective IgG subclass deficiencies, such as Bruton type agammaglobulinemia. Increased IgG loss is seen in protein-losing enteropathies, nephrotic syndrome, and through the skin from burns. Increased IgG metabolism is found in Wiskott-Aldrich syndrome, myotonic dystrophy, and with anti-immunoglobulin antibodies. Monoclonal IgG increases in IgG myeloma.

Modifications of currently available technology such as capillary zone electrophoresis are beginning to become available to the clinical laboratory. Such new technologies could serve as a screen in this algorithm replacing conventional SPEP.

The algorithm is for diagnosis. For subsequent monitoring the physician can order protein quantification of SPEP as a stand alone test.

4.11. Urinalysis Algorithm

In addition to plasma, proteins are found in several other body fluids and tissues, including urine, cerebrospinal fluid, anmiotic fluid, saliva and feces. By way of an example, the measurement of urinary proteins is described below.

The glomeruli behave as ultrafilters for the plasma proteins. In general transport of protein molecules through the glomerular membrane diminishes as protein size increases. The proportions of individual proteins excreted in the urine depend on the extent of their reabsorption by the renal tubes. Albumin represents approximately 60% of total protein excreted because it is not completely removed from the filtrate by the tubular cells. The low-molecular-weight proteins are actively reabsorbed from the filtrate and catabolized in the proximal tubule. Only a small amount of protein is excreted normally (20–150 mg/d), and most of it is albumin. Increased permeability of the glomeruli is therefore first signaled by increased amounts of albumin in the urine, and further increase is demonstrated by the appearance in urine of proteins with increasingly greater molecular weights.

There are four ways, in addition to hemorrhage, in which proteinuria can occur: 1) increased glomerular permeability in which the urine protein is mainly albumin, 2) defective tubular reabsorption in which the urinary proteins are mainly normal low molecular weight plasma proteins; increased concentration in the plasma of an abnormal low-molecular-weight protein such as immunoglobulin light chains; and 4) abnormal secretion of protein into the urinary tract.

Quantitative assay for total protein or for individual proteins is usually performed on timed collections.

FIG. 12 is a diagram illustrating the urinalysis algorithm with the follow-up (n+1)st test dependent on the result of the nth assay; the algorithm provides for quantitative urine chemistries which in negative samples is further continuted to measure protein, blood, leukocyte esterase or nitrite.

The urinalysis (UA) is one of the most commonly ordered tests in the clinical laboratory. Historically a series of semi-quantitative (results reported as 0, 1+, 2+, etc.) urine chemistry tests were performed and this was followed by a microscopic examination of the urine sediment, a very labor intensive and time consuming process. For a discussion of the classical examination of the urinary sediment and its clinical correlation (M. H. Haber, *Urinary Sediment: A Textbook Atlas*. (Chicago: Am. Soc. Clin. Pathol.), 1981.)

The recent availability of new technology which allows for quantitative urine chemistries to be performed off high speed chemistry analyzers with defined reference ranges makes the examination of the urine sediment under the light microscope essentially superfluous. This technology is commercially available and can be readily acquired by clinical laboratories. The one exception would be in children. Positive urine chemistry results for protein, blood, leukocyte esterase or nitrite would be rare in children and would raise the issue of possible abuse. A microscopic examination of the urine sediment to further examine this possibility might be useful.

The algorithm developed reduces the incidence of urine microscopics while allowing clinicians more accurate diagnostic/monitoring chemistry results with faster throughput and turn-around times.

Another possible application for this technology it for the screening of sterile urines with those specimens having positive chemistry test for protein, blood, leukocyte esterase or nitrite being reflexed to bacterial culture, (E. S. Pearlman et al, *Can Urine Chemistry Predict the Outcome of Urine Culture? An Assessment Using Discriminant Analysis* Presented at American Society Microbiology [98th General Meeting (1998)].

This system enables the user to dramatically increase productivity (depending on the analyzer, up to 16,000 tests per hour) versus manual and dipstick analyzers.

The principle of Individual assay is described below:

pH: This test is based on an indicator that gives a broad range of color intensity covering the entire pH range.

Specific Gravity: This test is based on the apparent pKa change of certain pretreated polyelectrolytes in response to ionic concentration of the test sample. The color change ranges from deep green to yellow with increasing ionic concentration.

Glucose: Glucose detection is based on an enzymatic reaction. This method was first described by Banauch in 1975 for the determination of glucose in urine. The glucose test of this system is a further development of that test principle. The reaction utilizes an enzyme to catalyze the formation of gluconic acid, and a hydrogen ion from the oxidation of glucose in the presence of a coenzyme. The coenzyme is reduced by the hydrogen ion, and this change is measured by spectrophotometry.

Protein: The test for the detection of protein in urine employs an indicator dissolved in an acid medium which reacts with protein to form a color protein-dye complex. The amount of color produced is proportional to the protein concentration. This method was first dscribed by Bannach in 1976. The protein test of this system is a further development of the Bradford Test principle.

Nitrite: This test depends on the conversion of nitrate (derived from the diet) to nitrite in the urine by the action of Gram negative bacteria. Nitrite, if present, reacts with the reagent aromatic amine to form a diazonium salt which couples with an indicator form a colored complex.

Ketones: This test is based on the development of color due to the reaction of acetoacetic acid with nitroprusside.

Blood (Hb): The chemical detection of blood is based on the strong pseudoperoxidase action of hemoglobin in erythrocytes. Numerous methods are described in the literature, which include various substrates (peroxides) and chromogens. Hemoglobin and myoglobin, if present, catalyze the oxidation of the indicator by the organic peroxide resulting in color development.

Leukocyte Esterase (LE): Leukocytes in urine are detected by the action of esterase, present in granulocytes. The esterase catalyzes the hydrolysis of the reagent amino acid ester resulting in the liberation of a chromophore that produces color.

Bilirubin: The detection of bilirubin is based on the coupling reaction of a diazonium salt with bilirubin in an acid medium containing a surfactant to yield a measurable color reaction.

Urobilinogen: The detection of urobilinogen is based on the coupling reaction of a diazonium salt with urobilinogen in an acid medium containing a surfactant to yield a measurable color reaction.

4.12. Human Immunodeficiency Virus Algorithm

Human immunodeficiency virus (HIV) infects a wide variety of tissues in humans; including bone marrow, lymph node, blood, brain, skin and bowel. HIV infection can induce cytopathic effects or apoptosis in some instances and latent and persistent infections in others, depending on the particular strain of virus. HIV-1 was isolated first from AIDS patients in the United States. HIV-2 was isolated from West African AIDS patients and is prevalent in Europe, Brazil, India and the U.S. While HIV-2 isolates exhibit several characteristics in common with HIV-1, HIV-2 is 3 times less efficient at being transmitted vertically. HIV can induce immunosuppression and AIDS but the viral load in individuals infected with this virus is much lower than found in HIV-1 infected people. HIV-2 can be serologically and molecularly distinguished from HIV-1.

Blood samples routinely collected by venipuncture, are generally used for viral detection and serologic analyses. To isolate virus from peripheral blood mononuclear cells, heparinized or EDTA—treated blood samples must be collected. HIV can also be detected in and isolated from other body fluids such as plasma, serum, cerebrospinal fluid, saliva, tears, milk, urine, and general secretions from biopsy specimens of infected tissues such as the bowel. Even though the amount of virus present in some biopsy specimens may be low, precautions should be taken when handling any potentially HIV-infected clinical specimens. Gloves should be worn, and needles should be handled by safe procedures after collection of blood.

Plasma, serum, or other body fluids to be tested serologically should be stored at −20 or −70° C. For best results, virus isolates should be performed immediately following specimen collection. For later detection of viral antigens, clinical specimens should be preferably stored at −70° C. Peripheral blood mononuclear cells and other infected cells may be stored in liquid nitrogen in culture medium plus 10% dimethyl sulfoxide.

Laboratories involved in HIV antibody testing should use biosafety level 2 standard. Clinical specimens from all individuals should be considered infected so as to avoid the confusion of having certain specimens handled differently. A class II type A biosafety cabinet with HEPA-filtered air should employed for viral isolation work. Gloves (two pairs) and a surgical gown should be worn.

Detection of HIV antibodies is still the most efficient and most common way to determine whether an individual has been exposed to HIV and to screen blood and blood products for this infectious agent.

A test is considered positive when assays such as the enzyme-linked W immunosorbent assay (ELISA), indirect immunofluorescence assay (IFA), and Western blots (immunoblots) are considered reactive. Increasing levels of virus-specific antibody can be quantified by a variety of serologic detection methods:

TABLE

Commercial Kits For HIV Testing

| Assay | Commercial Name | Company |
|---|---|---|
| Screening assays: | | |
| ELISA for HIV-1, using virus lysate | HIVAB HIV-1 EIA | Abbott Laboratories |
| | Enzygnost Anti-HIV | Behringwerke |
| | Retro-Tek HIV ELISA | Cellular Products |
| | DuPont ELISA | DuPont NEN |
| | HIV-1 ELISA | Diagnostic Biotechnology |
| | LAV EIA | Genetic Systems/Sanofi |
| | Ortho HIV ELISA | Ortho Diagnostic System |
| | Vironostika HIV-1 Microelisa System | Organon Teknika Corporation |
| ELISA for HIV-1, using recombinant proteins or synthetic peptides | HIVABp24 (rDNA) | Abbott Laboratories |
| | Recombigen (env & gag) HIV-1 EIA | Cambridge Biotech |
| | DuPont HIV-1 Recombinant | DuPont NEN |
| | HIV-1 env Peptide EIA | Labsystems |
| | UBI ELISA | United Biomedical International |
| ELISA for HIV-1 and HIV-2 | HIVAB HIV-1/HIV-2 (rDNA) EIA | Abbott Laboratories |
| | Recombigen HIV-1/HIV-2 EIA | Cambridge Biotech |
| | HIV-1/HIV-2 EIA | Genetic Systems/Sanofi |
| | Enzygnost Anti-HIV-1/2 Plus | Behringwerke |
| | Vironostika HIV-1 + 2 | Organon Teknika Corporation |
| Other rapid tests | Retro Cell | Abbott Laboratories |
| | Serodia-HIV | Fujirebio Inc. |
| | SUDS HIV-1 | Murex |
| | Recombigen HIV-LA | Cambridge Biotech |
| | SimpliRed | Agen |
| | Sero-Strip or Hema-Strip HIV-1/2 | Saliva Diagnostic Systems |
| Confirmatory assays: | | |
| Western blot assay | Novapath HIV-a Immunoblot | Bio-Rad Laboratories |
| | HIV-1 Western Blot | Cambridge Biotech |
| | HIV-1 Western Blot | Ortho/DuPont |
| | HIV-1 Western Blot | Epitope/Organon Teknika Corporation |
| | Genetic systems/Sanofi HIV-2 Western Blot | Genetic Systems/Sanofi Cambridge Biotech |
| IFA | Fluorognost HIV-1 IFA | Waldheim Pharmazeutica |
| | Virgo IFA | Pharmacia |
| | Retro-Tek IFA | Cellular Products |
| Line immunoassay p24 antigen assay | RIBA HIV-1/HIV-2 SIA | Chiron Corporation |
| | Liatek HIV-1/2 | Organon Teknika Corporation |
| | HIV-1 p24 Antigen Assay | Coulter Corporation/Immunotech, Inc. |
| | HIVAG-1 Monoclonal | Abbott Laboratories |
| | HIV-1 p24 ELISA | DuPont NEN |
| | Vironostika HIV-1 Antigen Screen | Organon Teknika Corporation |
| | ELAVIA Ag1 | Genetic Systems/Sanofi |
| | p24 EIA | Cellular Products |
| | p24 Antigen | Wellcome Diagnostics |

A positive test result indicates exposure and, outside of the perinatal and neonatal periods, is presumed to indicate infection by HIV.

Figure 15:
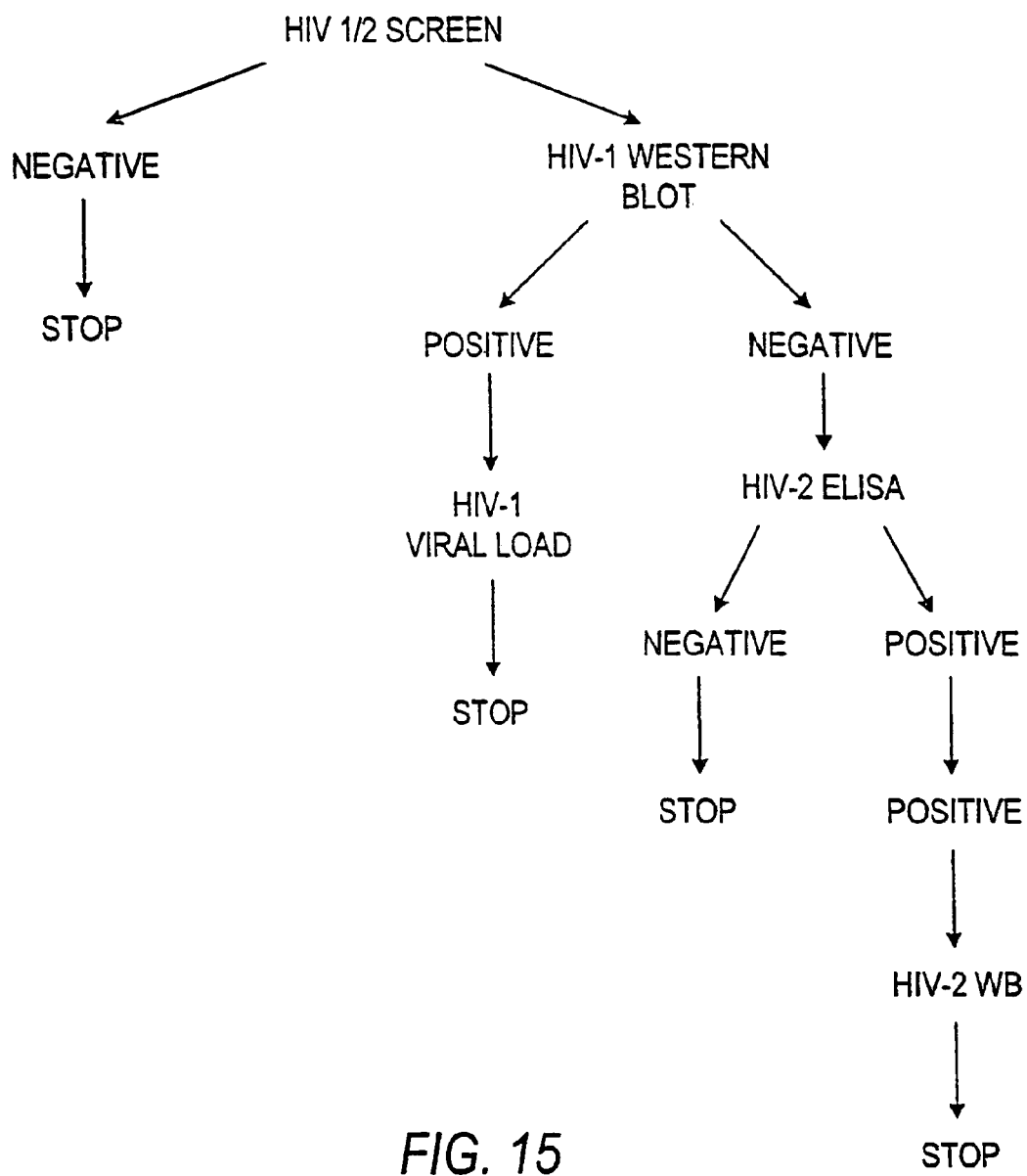
FIG. 15 is a diagram illustrating the human immunodeficiency with the follow-up (n+1)st test dependent on the result of the nth assay.

FIG. 15 describes the algorithm for testing HIV.

The AIDS epidemic continues and is complicated by the emergence of new strains of HIV. In the past laboratories have had to deal mainly with the HIV-1 virus but in recent years the HIV-2 strain has emerged. The CLS HIV algorithm is one of the first to use a screening test for diagnosis which is sensitive to both HIV-1 and 2. The use of such a screening test has in the past been confined to Blood Banks. In that arena the HIV-1/2 assay has been used for screening blood units rather than for patient diagnosis.

The FHV-1/2 screening tests as well as the Western Blot confirmatory test detect antibodies to the HIV virus. For purposes of monitoring therapy a direct measure of viral burden is desirable. The CLS algorithm would permit such a determination at the time of diagnosis. This would avoid a patient recall that is the norm under current diagnostic protocols.

Unfortunately because of HIV-2 is still a relatively rare occurrence in the United States a direct measurement of HIV-2 viral burden is not available. Also, an HIV-2 Western Blot assay is only available through a manufacturer's reference laboratory. The referral laboratory used by CLS is also the facility used by the New York State Department of Health. This reference laboratory is available to be used by the general clinical laboratory. Hopefully, assays will become commercially available for the FHV-2 Western Blot and Viral Load assays in the near future. The concept embodied in the algorithm however remains valid.

Genetic Systems™ HIV-1/HIV-2 Peptide EIA is the Genetic Systems Corporation qualitative enzyme immunoassay for the detection of circulating antibodies to Human Immunodeficiency Virus Type 1 (HIV-1) and/or Human Immunodeficiency Virus Type 2 (HIV-2) in human serum or plasma, and is indicated as a screening test for serum or plasma and as an aid in the diagnosis of infection with HIV-1 and/or HIV-2.

4.13 Syphilis Algorithm

Syphilis is still a common sexually transmitted disease in many areas of the world despite the availability of effective therapy. Transmission of the treponematoses occurs through direct contact with active lesions.

The current laboratory tests for syphilis fall into three categories: direct microscopic examination used when lesions are present; nontreponemal tests used for screening; and treponemal test which are confirmatory. In the United States, the routine testing scheme is direct microscopic examination of lesions exudates followed by a nontreponemal test that if reactive is confirmed with a treponemal test.

Criteria for syphilis are divided into three categories: definite, presumptive and suggestive.

FIG. 17 is a diagram illustrating the syphilis algorithm with the follow-up (n+1)st test dependent on the result of the nth assay; the algorithm comprises an automated objective assay for specific antibodies against the specific organism Treponemal specific screen; the positive samples are reflexed to an RPR; a positive RPR is a useful guide to therapy; a negative RPR indicates a discrepancy and may indicate either previously treated or late stage syphilis.

Syphilis remains a significant public health problem. Details may be found in any standard textbook of Medicine or Public health (J. C. Bennet and F. Plum (eds), *Cecil. Textbook of Medicine,* 20th edition (Philadelphia; W B Saunders), 1996.) Historically, the diagnosis of syphilis has been made serologically i.e., by assaying for antibodies to the causative organism (*T. pallidum*) rather than the organism itself. The usual screening test is an assay for antibodies to a lipid antigen derived from cell membranes which is released as a result of cell injury secondary to infection. This is the so called RPR (rapid plasma reagin) test. This assay is semi-quantitative. Positive results are reported as the highest dilution of the patient sample at which the result become negative. The more antibody is present, the higher the dilution (titer) required to produce a negative result. Unfortunately the RPR test is not specific for syphilis and frequently become non-reactive in later stages (so called latent and tertiary syphilis) of the disease even in the absence of treatment. Moreover interpretation of the test depends on the subjective evaluation of an agglutination reaction. One advantage of the test however, is that if it is reactive and the patient is treated it will become non-reactive or at least the titer will decrease.

In the traditional mode of testing, a reactive result on the RPR was followed by a test for antibodies directed specifically against antigens derived from the *T. pallidum* itself. This test is usually performed by a method that uses subjective interpretation of images under the fluorescence microscope. These antibodies once produced linger for many years even if the infection is treated.

The algorithm reverses the usual mode of operation. An automated, objective (based on readings of optical density) assay for specific antibodies against the organism is done (E. S. Pearlman et al, *Clin. Chem.* 44:1790 (1998)). This test detects those individuals with late stage disease who are frequently RPR non-reactive while a negative test is sufficient to rule out syphilis.

Those patients who are positive by the treponemal specific screen are reflexed to an RPR. If the RPR is reactive, its intensity (measured by titer) is a useful guide to therapy for the clinician. If the RPR is non-reactive an interpretive footnote is appended indicating that the discrepancy may indicate either previously treated or late stage syphilis.

RPR Card antigen suspension is a carbon particle cardiolipin antigen which detects "reagin", an antibody-like substance present in serum or plasma from syphilitic persons, and occasionally in serum or plasma of person with other acute or chronic conditions. The reagin binds to the test antigen, which consists of cardiolipin-lecithin-coated cholesterol particles, causing macroscopic flocculation.

Microtitration wells coated with *T. Pallidum* antigens are exposed to test specimens which may contain specific antibodies. After an incubation period, unbound components in the test sample are washed away. Specifically-bound IgG reacts with a biotinylated anti-human IgG monoclonal antibody bound with streptavidin-horseradish peroxidase (HRP) during a second incubation period. Following a second wash cycle, specifically-bound enzyme conjugate is detected by reaction with hydrogen peroxide and the chromogen tetramethylbenzidine (TMB). The assay is measured spectrophotometrically to indicate the presence or absence of IgG treponemal antibodies.

4.14 Intelligent Programming Algorithm: The concept of the algorithm from a systems point of view is described in FIG. 18. The result is compared by the computer with a rule which tells it whether and what test to order next in the sequence. The nature of the rule depends on whether the nth assay generates a qualitative result (positive, negative or equivocal) or a quantitative (numerical) result. In the latter case actual results may be compared with the "reference range" for the healthy population.

This reference range can be developed in several different ways although CLS currently uses a curve fit routine (H. Martin et al, *Normal Values in Clinical Chemistry* (New York: Marcel Dekker, 1975). On the basis of the qualitative result or by comparison of the patient result with the reference range, the computer will stop or order the appropriate (n+1)st assay in the sequence.

In the present invention, the rules are applied through an expert system which is an intrinsic part of the architecture of the laboratory computer system. This expert system is an event-driven, expert rule based, decision-support software within the Cerner system.

The system helps to define clinical rules that are applied to patient data that is generated or captured within the computer system. Rules are created by the application of a series of if then statements that are applied to test orders or generated results, to trigger new downstream events or orders. An example of the rule-formulating process is described below. It is of course, to be appreciated that different computer systems may handle the process of including if-then statements in different ways. The principle however, of applying such rules to the development of clinical laboratory algorithms remains valid.

FIG. 18 describes the system algorithm or the intelligent programming algorithm.

The following Example is designed to demonstrate how to create a rule from a given set of circumstances, and then compare the solution to ones created by Cerner. The Example is intended to serve as an illustration and may not reflect the best clinical means to accomplish the stated task.

EXAMPLE

The manager of the chemistry section of the laboratory wants to automate the ordering of follow-up LDH ISO enzyme (LDH ISOS). Currently the technologists must remember to order LDH ISOS for all patients if the result of the LDH is high. The established value regarded as "high" is 100. Three doctors however, have different criteria for high. Doctor Jones wants to order the LDH ISOS automatically if the LDH is greater than 95. Doctor Brown wants the LDH ISOS ordered if the LDH is greater than 92, and Doctor Carson considers 97 to be high.

The following questions should be addressed as one develops a solution:

Can one combine all of these criteria into one rule?

How does one address doctor-specific values?

Solutions to Example

All of the criteria mentioned can be combined. There are several ways to solve the problem presented in Example 1.

If you can use the admitting doctor to check the ordering doctor, use the Patient Demo premise definition function, as shown in the first solution. The other two solutions show the methods of handling the doctor-specific attribute.

Solution 1 to Example

|     | RESULT VALUE | LDH H   | [000 MIN, E, V] V1 Y ENTER ORDER LDH ISO V1 |
|-----|--------------|---------|---------------------------------------------|
| OR  | RESULT VALUE | LDH>95  | [000 MIN, E, V] V1 Y                        |
| AND | PATIENT DEMO | ADM DOC | "Dr. Jones"                                 |
| OR  | RESULT VALUE | LDH>92  | [000 MIN, E, V] V1 Y                        |
| AND | PATIENT DEMO | ADM DOC | "Dr. Brown"                                 |
| OR  | RESULT VALUE | LDH>97  | [000 MIN, E, V] V1 Y                        |
| AND | PATIENT DEMO | ADM DOC | "Dr. Carson"                                |

The logical sequence in which these premises are considered is important to the concept of rule writing. In Solution 1, the system is given seven lines to consider. The AND/OR groups are considered by Discern Expert as follows:

| | |
|---|---|
| Line 1: | RESULT VALUE LDH H [000 MIN, E, V] V1 Y . . . |
| | The first line is considered by the system and the truth of the line is determined. The line states, "If a result value for LDH is recognized, and it is high (premise), order an LDH ISO (conclusion)." This premise is good for all patients except those of the three doctors who have specified different criteria for what is to be regarded as "high". |
| | For the purposes of explaining this rule, assume that the actual clinical event that triggered the rule was an LDH result value of 98n for a patient named Fred Bloggs, who is Dr. Carson's patient. This being the case, the premise of the first line will not be true, since the department's established criteria for LDH high is 100. The system, however, is instructed to look at another premise first. |
| OR | |
| Line 2: | RESULT VALUE LDH H > 95 [000 MIN, E, V] V1 Y . . . |
| | This is true. The result is greater than 95, but the rule cannot execute the conclusion yet. The system is instructed to consider another premise. |
| AND | |
| Line 3: | PATIENT DEMO ADM DOC "Dr. Jones" |
| | In this scenario, the event was triggered by Dr. Carson's patient, so this group was not true, and the system must look still further. The OR that precedes the next premise ensures that the premise will be considered. |
| OR | |
| Line 4: | RESULT VALUE LDH > 92 [000 MIN, E, V] V1 Y |
| | This premise is true, but again, it is qualified by the AND statement that follows it. Like the second and third lines, when the system considers an AND statement, for this premise to be true, and the whole premise must be true. |
| AND | |
| Line 5: | PATIENT DEMO ADM DOC "Dr. Brown" |
| | This premise is not true. The system sees the OR statement following this premise and considers the next group. |
| OR | |
| Line 6: | RESULT VALUE LDH H > 97 [000 MIN, E, V] V1 Y . . . |
| | This premise is true. |
| AND | |
| Line 7: | AND PATIENT DEMO ADM DOC "Dr. Carson" |
| | This premise is true, too; therefore, the rule is true. The conclusion (ENTER ORDER LDH ISO) is executed. |

Solution 2 to Example

Another solution to Exercise 1 is shown below:

| | | | |
|---|---|---|---|
| | RESULT VALUE | LDH H | [000 MIN, E, V] V1 Y ENTER ORDER LDH ISO V1 |
| OR | RESULT VALUE | LDH>95 | [000 MIN, E, V] V1 Y |
| AND | ORDER STATUS | LDH BT 0 3 | [000 MIN, E, "Dr. Jones"] |
| OR | RESULT VALUE | LDH>92 | [000 MIN, E, V] V1 Y |
| AND | ORDER STATUS | LDH BT 0 3 | [000 MIN, E, "Dr. Brown"] |
| OR | RESULT VALUE | LDH>97 | [000 MIN, E, V] V1 Y |
| AND | ORDER STATUS | LDH BT 0 3 | [000 MIN, E, "Dr. Carson"] |

Solution 3 to Example

Another solution to Exercise 1, using the Result Status premise definition function to check the ordering doctor, is shown below:

| | | | |
|---|---|---|---|
| | RESULT VALUE | LDH H | [000 MIN, E, V] V1 Y ENTER ORDER LDH ISO V1 |
| OR | RESULT VALUE | LDH>95 | [000 MIN, E, V] V1 Y |
| AND | RESULT STATUS | LDH=4 | [000 MIN, E, "Dr. Jones"] |
| OR | RESULT VALUE | LDH>92 | [000 MIN, E, V] V1 Y |
| AND | RESULT STATUS | LDH=4 | [000 MIN, E, "Dr. Brown"] |
| OR | RESULT VALUE | LDH>97 | [000 MIN, E, V] V1 Y |
| AND | RESULT STATUS | LDH=4 | [000 MIN, E, "Dr. Carson"] |

It will thus be seen that the objects set forth above, among those made apparent from the preceding description, are officially obtained and, since certain changes may be made in carrying out the above method and the construction set forth without departing from the spirit and scope of the invention, it is intended that all matter contained in the above description and as shown in the accompanying drawings shall be interpreted as illustrative and not in a limiting sense.

It is also to be understood that the following claims are intended to cover all of the generic and specific structures of the invention herein described and all statements of the scope of the invention which, as a matter of language, might be said to fall there between.

What is claimed is:

1. A method of performing clinical diagnosis of Hepatitis B, comprising:
   a) submitting patient tests ordered by a physician to a clinical lab;
   b) selecting a Hepatitis B specific algorithm for tests necessary for clinical chemical analysis of Hepatitis B or any one of subgroups thereof;
   c) classifying the various subgroups of Hepatitis B, said classification based on pathology, pathogenic agent, cause and symptoms;
   d) defining a first set of relevant clinical tests suitable for diagnosing each of the subgroups of Hepatitis B classified in c), wherein the tests comprise HBsAg, HBsAb, and SGPT;
   e) carrying out only the relevant tests defined in d) to obtain at least one clinical test value followed by determination of a second set of relevant clinical tests;
   f) sequentially running the second set of clinical tests for each of the subgroups of Hepatitis B upon receiving a first set of said clinical test values, and computing a second set of clinical test values;
   g) repeating steps e) and f) with additional relevant clinical tests until a confirmed diagnosis of Hepatitis B and subgroup is provided.

* * * * *